(12) United States Patent
Hiraide et al.

(10) Patent No.: US 7,128,967 B2
(45) Date of Patent: *Oct. 31, 2006

(54) CALCIUM PHOSPHATE-SYNTHETIC RESIN-METAL COMPOSITE BODY AND METHOD FOR PRODUCTION THEREOF

(75) Inventors: Tsuneo Hiraide, Saitama-ken (JP); Yukio Kubota, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 245 days.

This patent is subject to a terminal disclaimer.

(21) Appl. No.: 10/621,680

(22) Filed: Jul. 18, 2003

(65) Prior Publication Data

US 2004/0071954 A1 Apr. 15, 2004

(30) Foreign Application Priority Data

Jul. 19, 2002 (JP) ............................. 2002-211690
Jun. 20, 2003 (JP) ............................. 2003-176747

(51) Int. Cl.
*B32B 5/16* (2006.01)
(52) U.S. Cl. ...................... 428/323; 428/327; 264/109; 264/112; 264/271.1; 264/279.1
(58) Field of Classification Search ................ 428/323, 428/327
See application file for complete search history.

(56) References Cited

U.S. PATENT DOCUMENTS

| | | | | |
|---|---|---|---|---|
| 3,787,900 | A | 1/1974 | McGee | .................. 424/422 |
| 4,192,021 | A | 3/1980 | Deibig et al. | ............ 623/23.61 |
| 4,222,128 | A | 9/1980 | Tomonaga et al. | |
| 4,904,534 | A | * | 2/1990 | Nagai | ......................... 428/457 |

FOREIGN PATENT DOCUMENTS

| | | |
|---|---|---|
| EP | 205333 | 12/1986 |
| EP | 962215 | 12/1999 |
| GB | 2010095 | 6/1979 |
| GB | 2216013 | 10/1989 |
| IE | 920833 | 3/1992 |
| JP | 63279835 | 11/1988 |
| JP | 2167868 | 6/1990 |
| JP | 848583 | 2/1996 |
| JP | 2002265795 | 9/2002 |

OTHER PUBLICATIONS

English Language Abstract of JP Appln. No. 2-167868.
English Language Abstract of JP Appln. No. 8-48583.
English Language Abstract of JP Appln. No. 2002-265795.

* cited by examiner

*Primary Examiner*—Monique R. Jackson
(74) *Attorney, Agent, or Firm*—Greenblum & Bernstein, P.L.C.

(57) ABSTRACT

A calcium phosphate-synthetic resin-metal composite body produced by pressing a metal member, calcium phosphate particles (or calcium phosphate particles and a calcium phosphate block) and synthetic resin particles I, which are at least partially cross-linked in advance, uncross-linked, synthetic resin particles II while heating, the calcium phosphate particles and/or the calcium phosphate block being exposed on at least part of the surface of the composite body. It is produced by (a) introducing a metal member, calcium phosphate particles (or calcium phosphate particles and calcium phosphate block), and synthetic resin particles I and II into a cavity of a molding die such that the synthetic resin particles surround the calcium phosphate particles, and that the calcium phosphate block, if any, is exposed on at least part of the composite body surface; and (b) pressing them in the molding die cavity while heating, so that the synthetic resin particles are bonded to the metal member and the calcium phosphate particles (or the calcium phosphate particles and the calcium phosphate block).

47 Claims, 29 Drawing Sheets

CALCIUM PHOSPHATE-SYNTHETIC RESIN-METAL COMPOSITE BODY AND METHOD FOR PRODUCTION THEREOF

FIELD OF THE INVENTION

The present invention relates to a calcium phosphate-synthetic resin-metal composite body having excellent workability and biocompatibility and usable as artificial dental roots, bone reinforcements, etc., and a method for producing such a composite body.

BACKGROUND OF THE INVENTION

Calcium phosphate is utilized for biomaterials such as artificial dental roots, bone reinforcements and dental cements because of excellent biocompatibility. However, it is poor in toughness due to its nature as a ceramic and cannot be used for members requiring impact resistance. Thus, artificial dental roots and bone reinforcements are made of metallic materials, which are not harmful to the human body, such as titanium and stainless steel. However, because calcium phosphate compounds, particularly hydroxyapatite, are much better in terms of biocompatibility, their use has been desired.

Under such circumstances, attempt has been made to combine calcium phosphate compounds with glass materials, metallic materials and synthetic resins, and some of the resultant composite bodies have been already put into practical use. However, when they are combined with the glass materials, there are problems that the glass elutes from the resultant composite bodies into the human body as time goes on, and that the composite bodies lack toughness.

Though attempt has been made to blend a molten synthetic resin and calcium phosphate particles to provide their composite body, the calcium phosphate particles easily collapse during blending, and the molten synthetic resin easily covers the calcium phosphate particles in the course of molding the composite body. In addition, burring disadvantageously occurs during grinding.

Known is a combination of a calcium phosphate-synthetic resin composite body with a calcium phosphate block to have improved biocompatibility. Though this composite body is excellent in workability, biocompatibility and water resistance, it does not have excellent impact resistance because of the use of synthetic resin particles as reinforcements.

The composite material composed of a calcium phosphate compound and metallic materials is generally obtained by burying calcium phosphate compound particles in a metal frame, or by sintering a mixture of metal powder and calcium phosphate compound powder. In the former case, however, the calcium phosphate compound is likely to move from the metal frame in a living body. In the latter case, the calcium phosphate compound particles exposed on the surface of the composite, sintered body are easily detached.

This application is related to Japanese Application No. 2002-200085, filed Jul. 9, 2002, and U.S. application Ser. No. 10/615,013, filed Jul. 9, 2003, still pending which claims priority of this Japanese application, the disclosures of which are incorporated by reference herein in their entireties.

OBJECTS OF THE INVENTION

Therefore, an object of the present invention is to provide a calcium phosphate-synthetic resin-metal composite body having excellent workability, biocompatibility and water resistance as well as high impact resistance.

Another object of the present invention is to provide a method for producing such a calcium phosphate-synthetic resin-metal composite body.

SUMMARY OF THE INVENTION

As a result of an intensive study in view of the above objects, the inventors have discovered that a composite body would be provided with further improved workability, biocompatibility, water resistance and impact resistance, if a metal member having excellent mechanical strength exists in a step of heat-pressing calcium phosphate particles (or calcium phosphate particles and a calcium phosphate block), synthetic resin particles I, which are at least partially cross-linked in advance, and uncross-linked, synthetic resin particles II. The present invention has been completed based on this finding.

Thus, the calcium phosphate-synthetic resin-metal composite body of the present invention is produced by pressing a metal member, calcium phosphate particles (or calcium phosphate particles and a calcium phosphate block), synthetic resin particles I, which are at least partially cross-linked in advance, and uncross-linked, synthetic resin particles II while heating, the calcium phosphate particles (or the calcium phosphate particles and the calcium phosphate block) being exposed on at least part of the surface of the composite body.

In the calcium phosphate-synthetic resin-metal composite body of the present invention, the synthetic resin particles I are softened while retaining their shapes to some extent, whereas the uncross-linked, synthetic resin particles II having thermoplasticity are softened or melted during pressing while heating. When the composite body contains a porous calcium phosphate block, the softened or molten synthetic resin particles preferably enter into pores of the calcium phosphate block. The metal member and calcium phosphate particles (or calcium phosphate particles and a calcium phosphate block) are firmly fixed in the composite body by bonding the synthetic resin particles to the metal member and the calcium phosphate particles (or the calcium phosphate particles and the calcium phosphate block).

In the calcium phosphate-synthetic resin-metal composite body, it is preferable that the synthetic resin particles I, which are at least partially cross-linked in advance, and the uncross-linked, synthetic resin particles II are bonded to each other. By pressing while heating, the synthetic resin particles I are softened while retaining the shapes to some extent for bonding, and the synthetic resin particles II are softened or melted to enter voids between the particles to form a calcium phosphate-synthetic resin composite body. The synthetic resin particles II filling voids between the particles act as binders.

In a normal condition, not only are the calcium phosphate particles firmly fixed by the synthetic resin particles I and II, but also the synthetic resin particles I and II are firmly bonded to each other. At the time of grinding and polishing, however, exfoliation occurs at interfaces between the calcium phosphate particles and the synthetic resin particles and at interfaces between the synthetic resin particles I and II. Therefore, the calcium phosphate-synthetic resin-metal composite body of the present invention has excellent workability.

A calcium phosphate-synthetic resin composite layer preferably covers the entire surface of the metal member. Particularly excellent in biocompatibility is the calcium phosphate-synthetic resin-metal composite body comprising a composite layer covering the entire surface of the metal member such that the metal member is not exposed.

The metal member is preferably made of a metal or an alloy selected from the group consisting of pure titanium, titanium alloys and stainless steel. At least part of the metal member preferably has a thickness of 0.5 mm or more. An example of preferable shapes of the metal member is a screw shape. In this case, a composite layer composed of calcium phosphate particles and synthetic resin particles I and II is preferably formed on a trunk of a screw.

The metal member is preferably in the form of a mesh. In this case, each side of the metal mesh is preferably covered with the calcium phosphate-synthetic resin composite layer. When the metal member is in the form of a mesh, the calcium phosphate-synthetic resin composite layer easily adheres to the metal member.

A further example of preferable shapes of the metal member is a hollow shape. In this case, the entire surface of the metal member is preferably covered with a hollow calcium phosphate-synthetic resin composite layer. When the hollow composite body is implanted in a living body, a bone material may be charged into the composite body. It is preferable that the metal member has a window, and that the calcium phosphate-synthetic resin-metal composite body has an opening in alignment with the window.

The calcium phosphate particles are preferably porous in terms of biocompatibility. The average particle size of the calcium phosphate particles is preferably 0.001 to 10 mm, and the calcium/phosphorus molar ratio is preferably 1.4 to 2.0. The calcium phosphate particles are preferably sintered in advance.

Both of the synthetic resin particles I and II are preferably made of a water-insoluble acrylic or polystyrene resin, particularly polymethyl methacrylate. The content of the uncross-linked, synthetic resin particles II is preferably 0.2 to 50% by mass based on the total amount of the synthetic resin particles I and II.

The mass ratio of the calcium phosphate particles to the synthetic resin particles in the calcium phosphate-synthetic resin-metal composite body is preferably 1/9 to 8/2.

When the calcium phosphate-synthetic resin-metal composite body comprises a calcium phosphate block, the calcium phosphate block is preferably porous in terms of biocompatibility. A calcium/phosphorus molar ratio in the calcium phosphate block is preferably 1.4 to 2.0. Also, preferably used from a practical standpoint is the sintered calcium phosphate block having a thickness of at least 1 mm.

The method for producing the calcium phosphate-synthetic resin-metal composite body of the present invention comprises the steps of (a) introducing a metal member, the calcium phosphate particles (or calcium phosphate particles and a calcium phosphate block), and synthetic resin particles I and II into a cavity of a molding die, such that the synthetic resin particles surround the calcium phosphate particles, and such that the calcium phosphate particles and/or the calcium phosphate block are present on at least part of a surface of the composite body; and (b) pressing them in a cavity of a molding die while heating, so that the synthetic resin particles are bonded to the metal member and the calcium phosphate particles (or calcium phosphate particles and a calcium phosphate block).

The calcium phosphate particles (and/or the calcium phosphate block) are preferably sintered. Its sintering temperature is preferably 500° C. to 1,300° C.

The step of pressing while heating is preferably carried out in vacuum or in an atmosphere containing no oxygen.

The method for producing the calcium phosphate-synthetic resin-metal composite body according to a preferable embodiment of the present invention comprises using a hollow metal member; pressing a mixture of the calcium phosphate particles and the synthetic resin particles I and II surrounding the metal member while heating to provide a composite body comprising the metal member embedded in a calcium phosphate-synthetic resin composite body; and grinding part of the calcium phosphate-synthetic resin composite body in the metal member-embedded composite body to provide a hollow calcium phosphate-synthetic resin-metal composite body.

In a preferable example of the above-described method, a hollow metal member having a window is used, and the calcium phosphate-synthetic resin composite body is partially cut by machining at a position aligned with the window to form a hollow calcium phosphate-synthetic resin-metal composite body having a window.

The method for producing a screw-shaped, calcium phosphate-synthetic resin-metal composite body according to another preferable embodiment of the present invention comprises using screw-shaped metal member; placing the metal member in a cavity of a molding die with a cap put on its thread; charging a mixture of the calcium phosphate particles and the synthetic resin particles I and II into the molding die cavity; pressing them while heating to form a calcium phosphate-synthetic resin composite body around the metal member; removing the cap from the thread of the screw; and threading the calcium phosphate-synthetic resin composite body around a trunk of the screw-shaped metal member.

Preferably used in the above method is a molding die comprising a stationary die member having a cavity extending in its entire length in a vertical direction; a lower punch having a cavity having a shape for receiving the capped, screw-shaped metal member and entering into the cavity of the stationary die member from its lower end; a protection die having a cavity extending in its entire length in a vertical direction and a cavity having a shape for receiving the capped, screw-shaped metal member, which abuts the lower punch; and a vertically movable upper punch having a cavity having the same shape as that of the cavity of the lower punch at a position aligned with the cavity of the lower punch, which enters into the vertical cavity of the protection die from above to abut the lower punch.

In a preferred embodiment, the capped, screw-shaped metal member is placed in the cavity of the lower punch; the lower punch is positioned in the cavity of the stationary die member; the protection die is caused to move downward so that the cavity of the protection die abuts the cavity of the lower punch; a mixture of the calcium phosphate particles and the synthetic resin particles I and II is charged into the combined cavities of the lower punch and the protection die; the upper punch is caused to move downward to press the mixture while heating, thereby forming the calcium phosphate-synthetic resin composite body around the trunk of the metal member.

DETAILED DESCRIPTION OF THE PREFERRED EMBODIMENTS

[1] Calcium Phosphate-synthetic Resin-metal Composite Body

The calcium phosphate-synthetic resin-metal composite body comprises calcium phosphate particles (or calcium phosphate particles and a calcium phosphate block), synthetic resin particles I, which are at least partially cross-linked in advance, and uncross-linked, synthetic resin particles II.

(1) Metal Member

The metal member is not limited as long as it has sufficient strength to function as reinforcement in the composite body and it is not harmful to the human body, and may be made of generally used materials. The metal member is preferably at least one metal or alloy selected from the group consisting of pure titanium, titanium alloys and stainless steel.

The metal member is preferably in a shape of column, cylinder, screw, mesh or plate. The outer diameter of the columnar metal member is preferably the same as or about 1 to 5 mm smaller than that of the calcium phosphate-synthetic resin-metal composite body. Though not particularly limited as long as the metal member is shorter than the calcium phosphate-synthetic resin-metal composite body, the height of the metal member is preferably about 0.5 mm to 100 mm. When the screw-shaped metal member is used, the outer diameter of the trunk of the screw is preferably 1 to 10 mm. When a cylindrical metal member is used, the thickness of the metal member is preferably 0.5 mm to 20 mm. When the thickness of the metal member is less than 0.5 mm, the metal member is not strong enough to function as reinforcement in the composite body. On the other hand, when the thickness of the metal member exceeds 20 mm, the composite body has low workability and biocompatibility.

The metal mesh is preferably constituted by wires having a diameter of 3 mm or less. The number of mesh openings is not particularly limited; the mesh openings may be small or large. To have improved adhesion to synthetic resins, the surface of the metal member may be subjected to an anchoring treatment, etc. before heat-pressing.

In the case of a plate-shaped metal member, it preferably has a thickness of about 0.5 to 5 mm. The metal member is preferably provided with a plurality of through-holes perpendicular to its plane. In a case where the plate-shape metal member is completely covered with the calcium phosphate-synthetic resin composite body, the calcium phosphate-synthetic resin composite layers on both sides of the metal member can be connected with each other via the through-holes. The through-holes are arranged preferably at an equal interval. A percentage of the through-holes to the metal member in area is preferably 5 to 90%. When the total area of the through-holes is less than 5%, the contact area of the calcium phosphate-synthetic resin composite layers is too small, resulting in easy peeling from the metal member. On the other hand, when it exceeds 90%, the metal member does not have enough strength as reinforcement.

Figure 12:
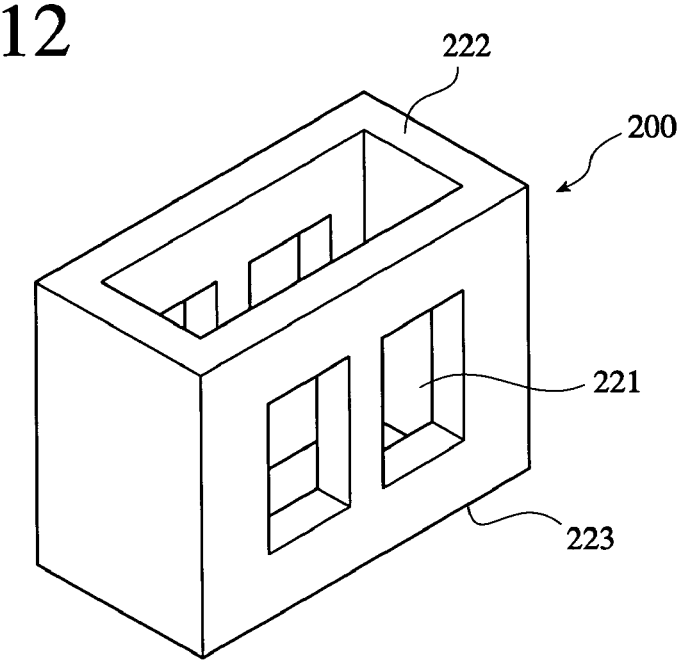
FIG. 12 is a perspective view showing one example of a metal member.

The metal member preferably (a) is hollow, (b) has an upper end and a lower end, at least one of which is open, and (c) has one or more windows. It is thus in a shape of a cylinder having a circular, oval or rectangular cross section. FIG. 12 shows one specific example of such metal member. This metal member 200 is a cylinder having a rectangular cross section having a pair of windows 221 in each sidewall. The cylindrical, windowed metal member can provide a cylindrical, windowed calcium phosphate-synthetic resin-metal composite body. When the cylindrical, windowed calcium phosphate-synthetic resin-metal composite body is implanted in a living body, osteoblasts and a body fluid easily enter into its hollow portion, so that the bone is easily regenerated around the composite body.

Though not particularly restrictive, the number of the windows in the metal member is practically 5 or less, preferably 4 or less in each surface in the case of the cylindrical calcium phosphate-synthetic resin-metal composite body having a rectangular cross section. The total area of the windows 221 is preferably 80% or less of the area of each sidewall. When the total area of the windows 221 is more than 80%, the metal member does not have enough strength as reinforcement for the composite body.

(2) Calcium Phosphate Particles

The calcium/phosphorus molar ratio in the calcium phosphate particles is preferably 1.4 to 2.0. Specific examples of the calcium phosphate particles include apatites such as hydroxyapatite and fluoroapatite, calcium phosphates such as tricalcium phosphate and tetracalcium phosphate, and mixtures thereof.

The calcium phosphate particles may be porous or non-porous particles, but porous ones are more preferable. In the case of porous calcium phosphate particles, their porosity is preferably 20 to 70%. Though the pores of the porous particles may be of various sizes, they preferably have diameters of 10 to 2000 μm.

It is preferable that the calcium phosphate particles have adjusted particle sizes so that their average particle diameter is 0.001 to 10 mm. The more preferable average particle diameter of the calcium phosphate particles is 0.01 to 6 mm. When the average particle diameter of the calcium phosphate particles is more than 10 mm, the calcium phosphate particles are easily detached from the calcium phosphate-synthetic resin-metal composite body during use. On the other hand, when it is less than 0.001 mm, they are easily agglomerated with poor dispersibility and suffer from a high cost. The average particle diameter may be measured by known methods.

The calcium phosphate particles are preferably sintered before pressing while heating. The sintering temperature is preferably 500 to 1300° C. and more preferably 700 to 1200° C. When the sintering temperature is below 500° C., the calcium phosphate particles are easily collapsed. Particularly in the case of the porous calcium phosphate particles, they are deformed and lose their porosity due to the crushing of pores by the application of pressure. When the sintering temperature is above 1300° C., the calcium phosphate compound is undesirably decomposed or deteriorated.

A sintering time, in which the above sintering temperature is kept, is preferably 1 to 10 hours. When the sintering time is less than 1 hour, the calcium phosphate particles would not exhibit a sufficient reinforcing effect even if sintered. On the other hand, even when the sintering time is more than 10 hours, no further effect is obtained, only resulting in increase in cost. The more preferable sintering time is 2 to 5 hours.

Though not particularly limited, a sintering atmosphere is preferably air to prevent the decomposition of the calcium phosphate particles.

(3) Synthetic Resin Particles

The synthetic resin particles comprise synthetic resin particles I, which are at least partially cross-linked in advance, and uncross-linked, synthetic resin particles II. The synthetic resin particles I, which are at least partially cross-linked in advance, and the uncross-linked, synthetic resin particles II are not limited as long as they are not harmful to the human body, and materials known in the art can be used therefor. The synthetic resin particles I and II preferably comprise a water-insoluble acrylic or polystyrene resin and the like, particularly polymethyl methacrylate. The same or different materials may be used for the synthetic resin particles I and II.

Each of the synthetic resin particles I and II has an average particle diameter of preferably 0.05 to 500 μm, more preferably 0.1 to 100 μm. Also, the average particle diameters of the synthetic resin particles are preferably smaller than that of the calcium phosphate particles.

The content of the synthetic resin particles II is preferably 0.2 to 50% by mass based on the total amount of the synthetic resin particles I and II. When the content of the synthetic resin particles II is less than 0.2%, the composite body is not sufficiently stable in water. On the other hand, when their content is more than 50% by mass, not only are the synthetic resin particles II likely to intrude into the porous calcium phosphate particles at the step of pressing while heating, but also the resultant composite body has low workability.

(4) Calcium Phosphate Block

The calcium phosphate-synthetic resin-metal composite body of the present invention may or may not contain a calcium phosphate block. When containing the calcium phosphate block, its composition is preferably the same as that of the calcium phosphate particles.

The calcium phosphate block may be porous or nonporous, though a porous one is more preferable. In the case of a porous calcium phosphate block, its porosity is preferably 5 to 90%. Though the pores of the calcium phosphate block may be of various sizes, they preferably have diameters of 20 to 2000 μm.

Though not particularly limited, the calcium phosphate block may be in a shape of a rectangular column or a circular column. Though not particularly limited as long as the calcium phosphate block is thinner than that of the calcium phosphate-synthetic resin-metal composite body, the thickness of the calcium phosphate block is preferably 1 mm or more from a practical standpoint.

(5) Structure of Calcium Phosphate-synthetic Resin-metal Composite Body

In the calcium phosphate-synthetic resin-metal composite body of the present invention, the calcium phosphate particles (or the calcium phosphate particles and the calcium phosphate block) are exposed on at least part of surface thereof.

Figure 13:
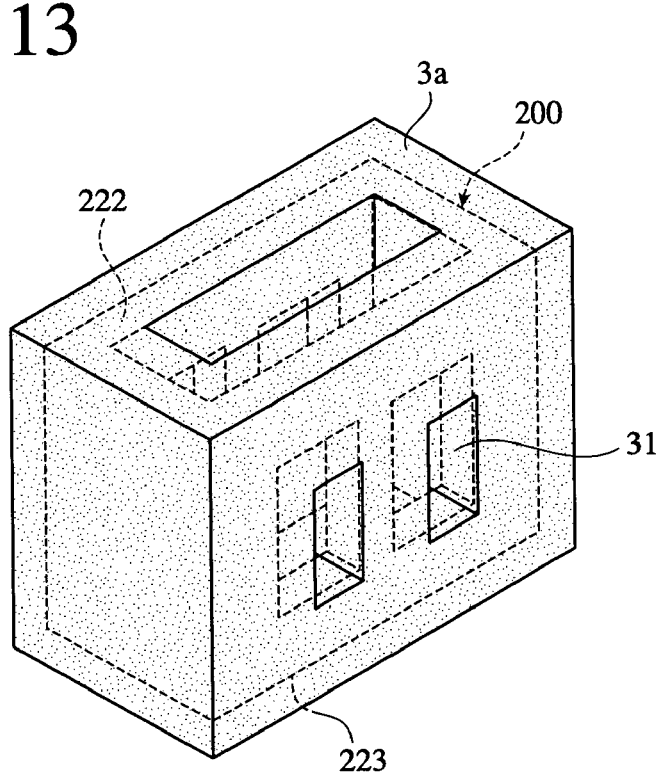
FIG. 13 is a perspective view showing a calcium phosphate-synthetic resin-metal composite body comprising the metal member shown in FIG. 12.

FIGS. 1 to 11 and FIGS. 13 to 15 show the calcium phosphate-synthetic resin-metal composite bodies according to various embodiments of the present invention without intention to limit the present invention thereto. Though not particularly limited, the calcium phosphate-synthetic resin-metal composite body may be in a shape of a rectangular column, a circular column, plate, cylinder, screw or a combination thereof. FIGS. 1 to 9 show examples of calcium phosphate-synthetic resin-metal composite bodies in a circular column shape. FIGS. 10 and 11 show examples of calcium phosphate-synthetic resin-metal composite bodies in a plate shape. FIGS. 13 and 14 show examples of calcium phosphate-synthetic resin-metal composite bodies in a cylinder shape. FIG. 15 shows an example of calcium phosphate-synthetic resin-metal composite body in a screw shape.

FIGS. 1 to 6 show examples of calcium phosphate-synthetic resin-metal composite bodies each comprising a calcium phosphate block. FIGS. 7 to 11 and FIGS. 13 to 15 show examples of calcium phosphate-synthetic resin-metal composite bodies each comprising no calcium phosphate block.

Figure 1A:
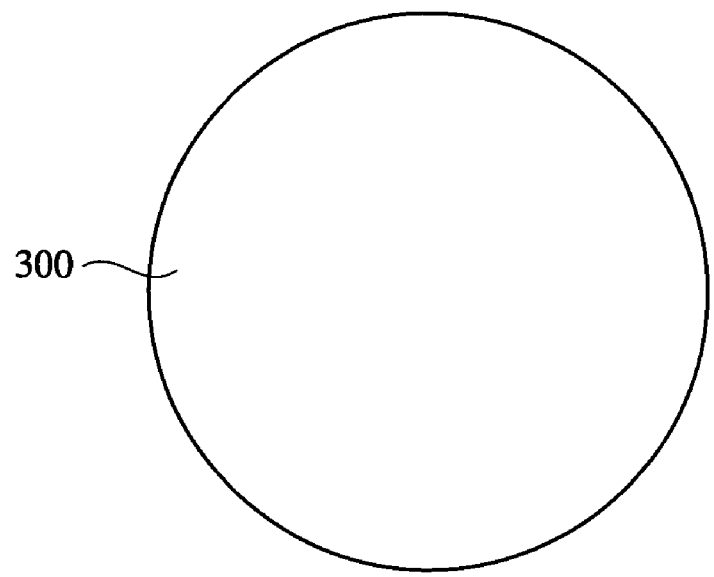
FIG. 1(a) is a top view showing one example of the calcium phosphate-synthetic resin-metal composite body of the present invention.
Figure 1B:
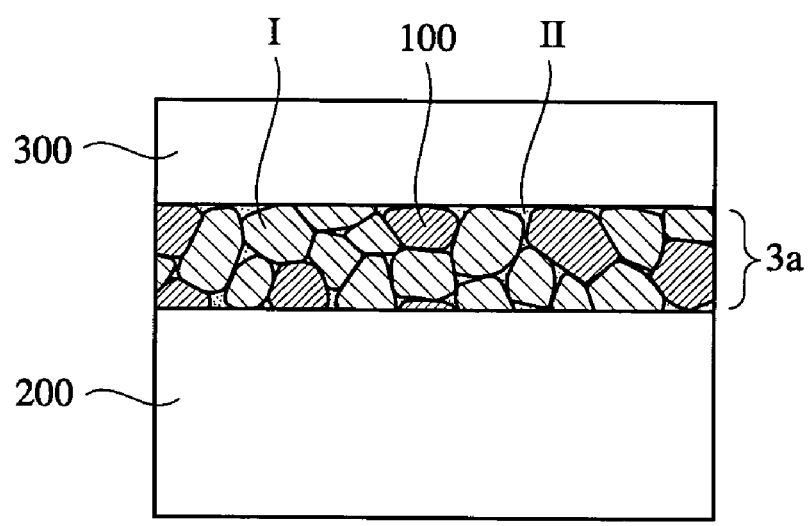
FIG. 1(b) is a side view showing the example shown in FIG. 1(a)
Figure 2A:
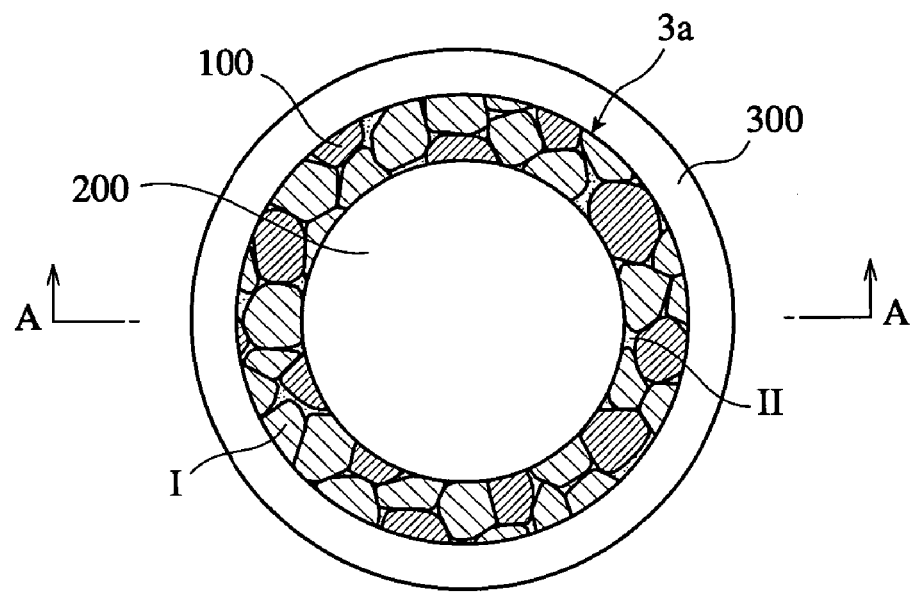
FIG. 2(a) is a top view showing another example of the calcium phosphate-synthetic resin-metal composite body of the present invention.
Figure 2B:
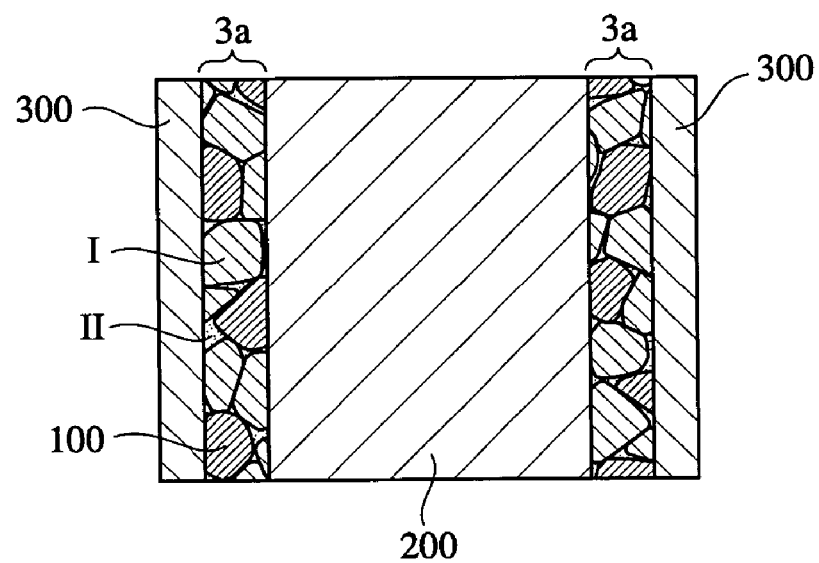
FIG. 2(b) is a vertical, cross-sectional view taken along the line A—A in FIG. 2(a)

FIG. 1(a) is a top view showing a calcium phosphate-synthetic resin-metal composite body, and FIG. 1(b) is a side view thereof. The calcium phosphate-synthetic resin-metal composite body shown in FIGS. 1(a) and 1(b) has a triple-layer structure comprising an upper layer constituted by a calcium phosphate block 300, a middle layer (a calcium phosphate-synthetic resin composite layer 3a) composed of a mixture of the calcium phosphate particles 100 and the synthetic resin particles, and a lower layer constituted by the metal member 200 adhering to the middle layer. The synthetic resin particles in the calcium phosphate-synthetic resin composite layer 3a are composed of synthetic resin particles I, which are at least partially cross-linked in advance, and uncross-linked, synthetic resin particles II. The cross-linked, synthetic resin particles I and the uncross-linked, synthetic resin particles II surround and tightly fix the calcium phosphate particles 100. The calcium phosphate particles 100 are exposed on the surface of the calcium phosphate-synthetic resin composite layer 3a.

In each of FIGS. 2 to 9, (a) is a top view showing a calcium phosphate-synthetic resin-metal composite body, and (b) is a vertical, cross-sectional view thereof. The calcium phosphate-synthetic resin-metal composite body shown in FIGS. 2(a) and 2(b) has a triple-layer structure comprising a cylindrical calcium phosphate block 300, a calcium phosphate-synthetic resin composite layer 3a contained therein, and a cylindrical metal member 200 contained in the calcium phosphate-synthetic resin composite layer 3a. The composition of the calcium phosphate-synthetic resin composite layer 3a may be the same as in the example shown in FIG. 1.

Figure 3A:
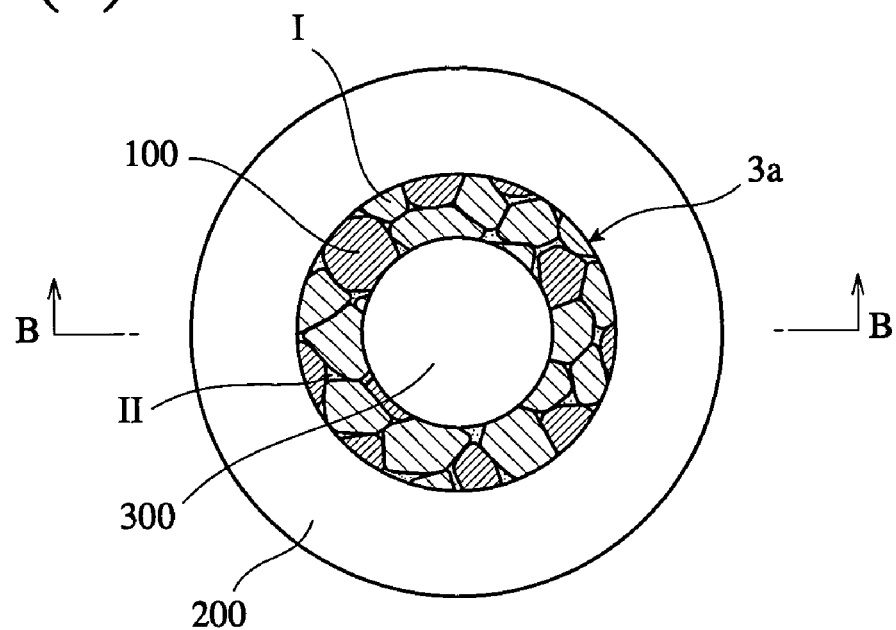
FIG. 3(a) is a top view showing a further example of the calcium phosphate-synthetic resin-metal composite body of the present invention.
Figure 3B:
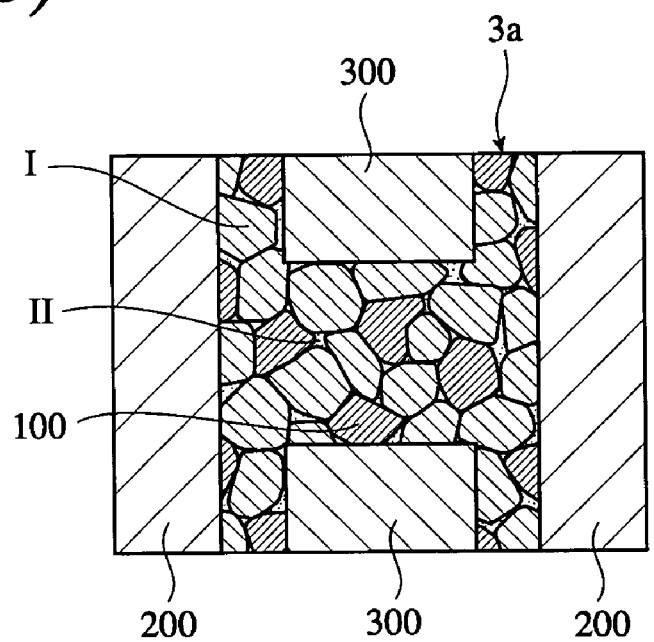
FIG. 3(b) is a vertical, cross-sectional view taken along the line B—B in FIG. 3(a)

FIGS. 3 to 5 show examples of calcium phosphate-synthetic resin-metal composite bodies each comprising a cylindrical metal member 200 covering a lateral surface thereof. The calcium phosphate-synthetic resin-metal composite body shown in FIGS. 3(a) and 3(b) has a structure comprising an outer layer constituted by a metal member 200, a calcium phosphate-synthetic resin composite layer 3a contained therein and two calcium phosphate blocks 300, 300 exposed on upper and lower surfaces of the composite body at a central of the calcium phosphate-synthetic resin composite layer 3a. The composition of the calcium phosphate-synthetic resin composite layer 3a may be the same as in the example shown in FIG. 1.

Figure 4A:
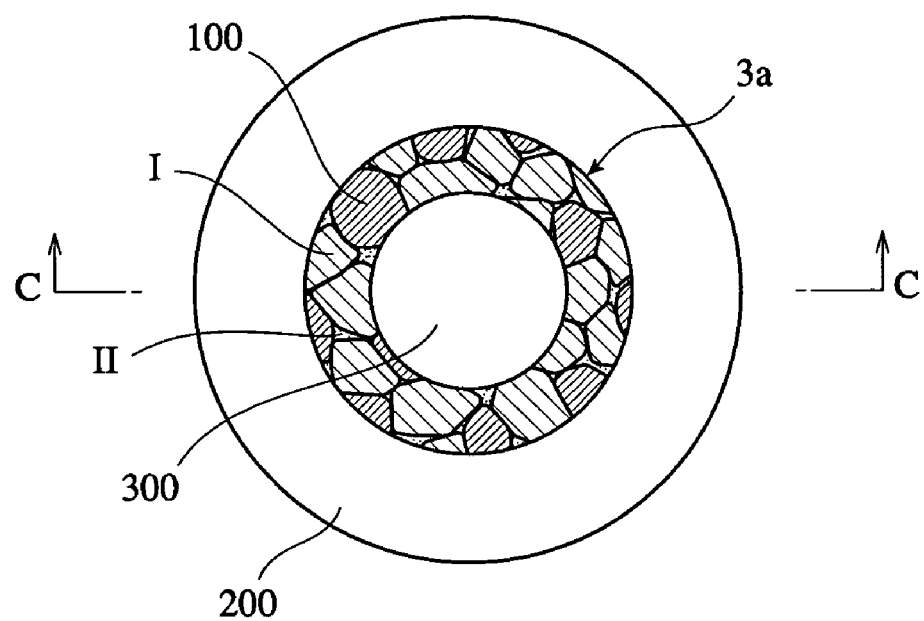
FIG. 4(a) is a top view showing a still further example of the calcium phosphate-synthetic resin-metal composite body of the present invention.
Figure 4B:
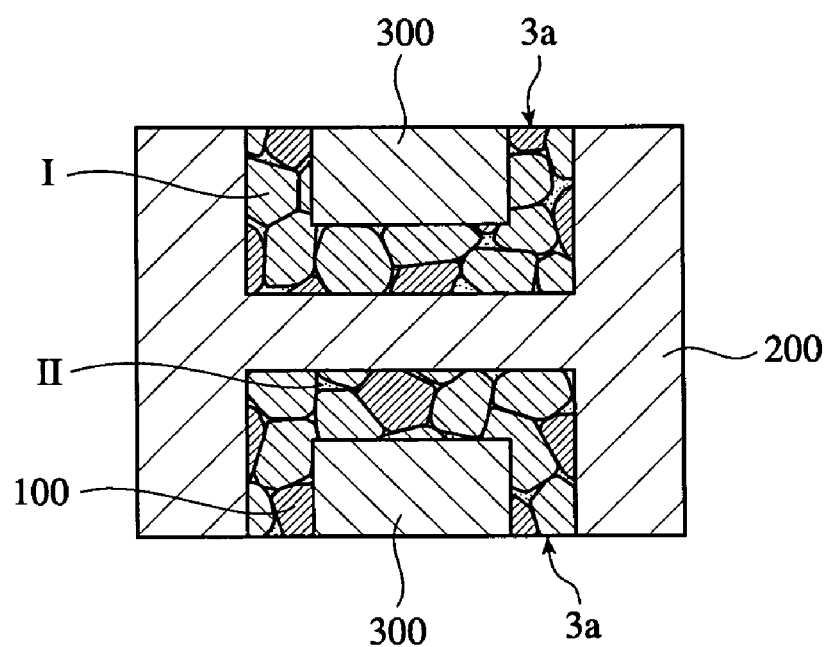
FIG. 4(b) is a vertical, cross-sectional view taken along the line C—C in FIG. 4(a)

The calcium phosphate-synthetic resin-metal composite body shown in FIGS. 4(a) and 4(b) has a structure comprising a metal member 200 having a center horizontal partition, two circular columnar calcium phosphate blocks 300, 300 arranged on both sides of the partition, and calcium phosphate-synthetic resin composite layers 3a charged between the partition of the metal member 200 and the calcium phosphate blocks 300, 300. In other portions, this composite body may be the same as that shown in FIG. 3.

Figure 5A:
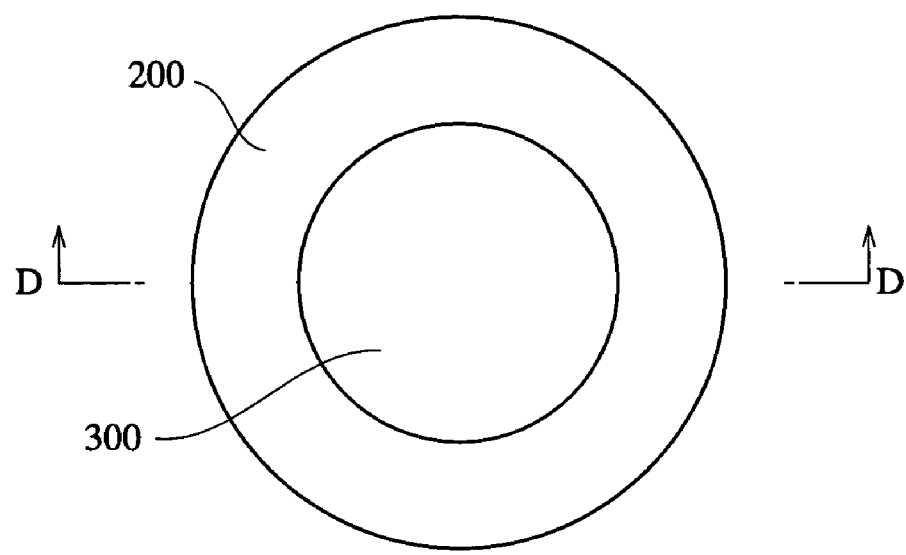
FIG. 5(a) is a top view showing a still further example of the calcium phosphate-synthetic resin-metal composite body of the present invention.
Figure 5B:
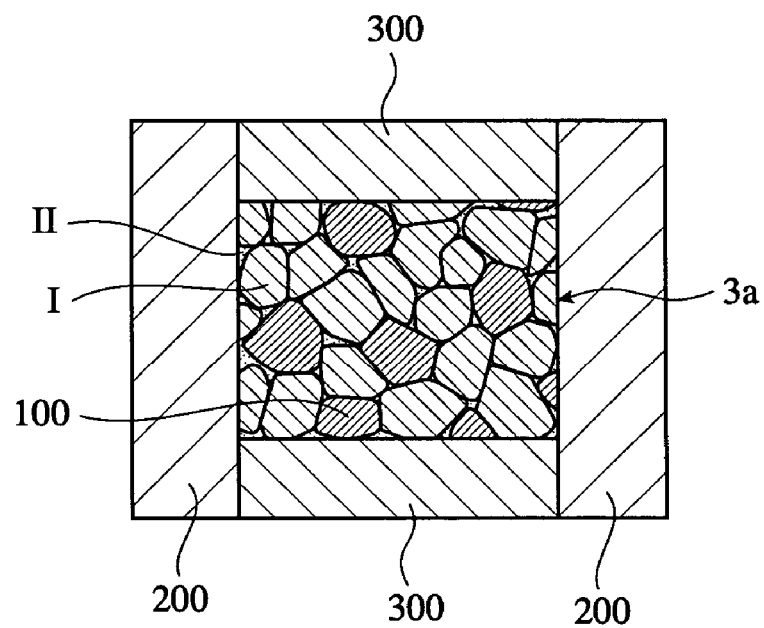
FIG. 5(b) is a vertical, cross-sectional view taken along the line D—D in FIG. 5(a)

The calcium phosphate-synthetic resin-metal composite body shown in FIGS. 5(a) and 5(b) has a structure comprising an outer layer constituted by a metal member 200, and an inner layer constituted by a calcium phosphate-synthetic resin composite layer 3a composed of a mixture of the calcium phosphate particles 100 and the synthetic resin particles and a pair of calcium phosphate blocks 300, 300 sandwiching the composite layer 3a. The composition of the calcium phosphate-synthetic resin composite layer 3a may be the same as in the example shown in FIG. 1.

Figure 6A:
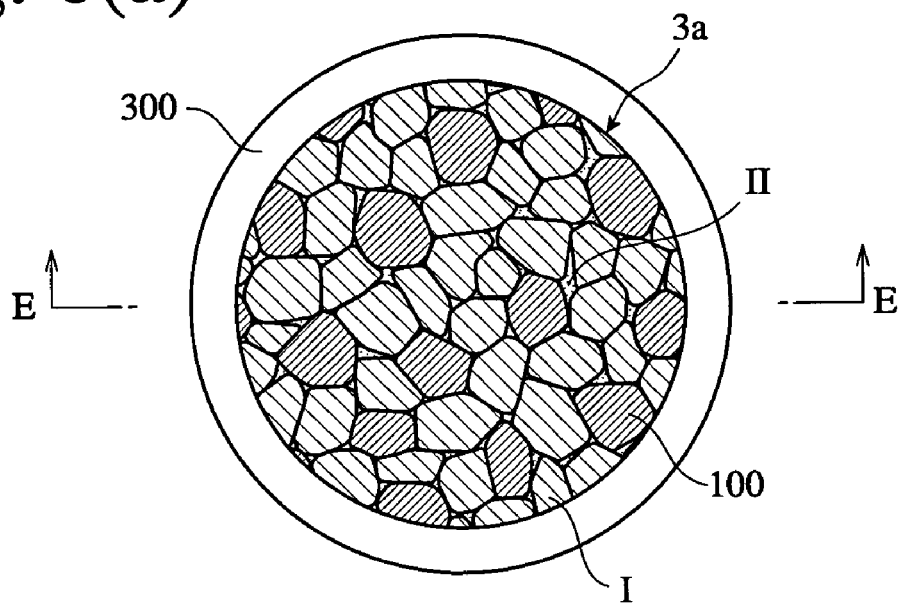
FIG. 6(a) is a top view showing a still further example of the calcium phosphate-synthetic resin-metal composite body of the present invention.
Figure 6B:
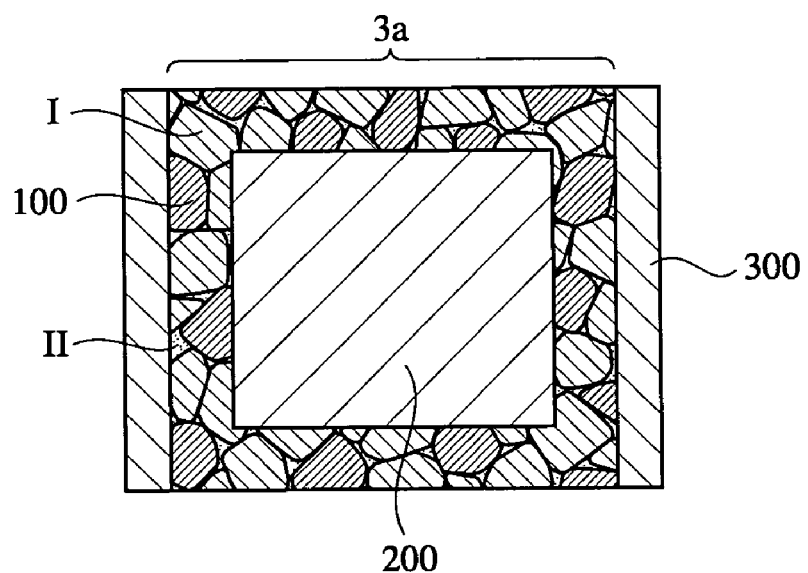
FIG. 6(b) is a vertical, cross-sectional view taken along the line E—E in FIG. 6(a)

The calcium phosphate-synthetic resin-metal composite body shown in FIGS. 6(a) and 6(b) has a structure comprising a cylindrical calcium phosphate block 300 (outer layer), a calcium phosphate-synthetic resin composite layer 3a (middle layer) contained in the calcium phosphate block 300, and a circular metal column 200 (inner layer) contained in the calcium phosphate-synthetic resin composite layer 3a. The calcium phosphate-synthetic resin composite layer 3a encloses the columnar metal member 200. The composition of the calcium phosphate-synthetic resin composite layer 3a may be the same as in the example shown in FIG. 1.

Figure 7A:
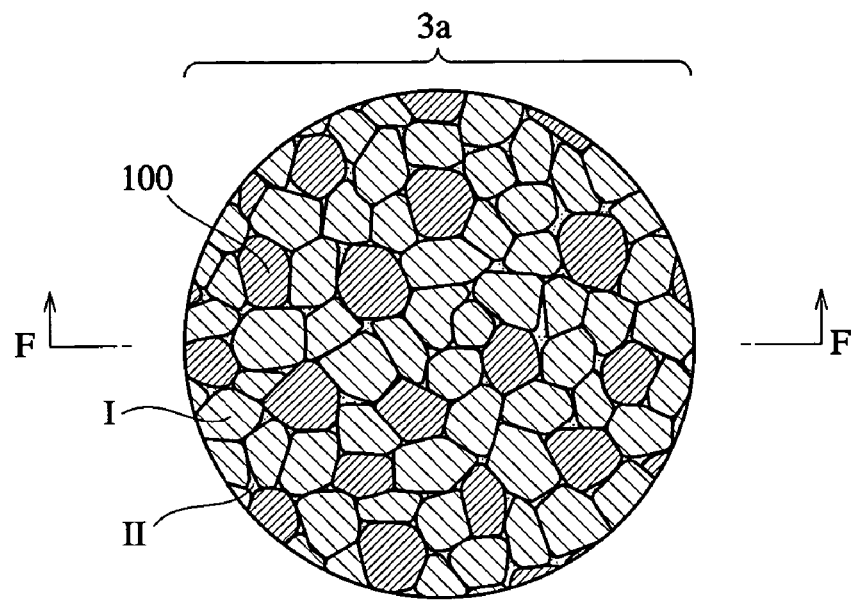
FIG. 7(a) is a top view showing a still further example of the calcium phosphate-synthetic resin-metal composite body of the present invention.
Figure 7B:
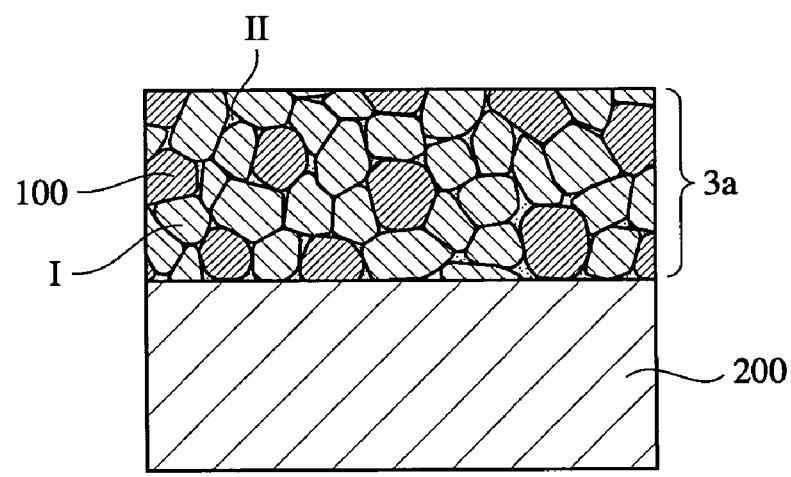
FIG. 7(b) is a vertical, cross-sectional view taken along the line F—F in FIG. 7(a)

The calcium phosphate-synthetic resin-metal composite body shown in FIGS. 7(a) and 7(b) has a double-layer structure comprising a calcium phosphate-synthetic resin composite layer 3a and a layer constituted by a metal member 200 adhering to a lower surface of the calcium phosphate-synthetic resin composite layer 3a. The composition of the calcium phosphate-synthetic resin composite layer 3a may be the same as in the example shown in FIG. 1.

Figure 8A:
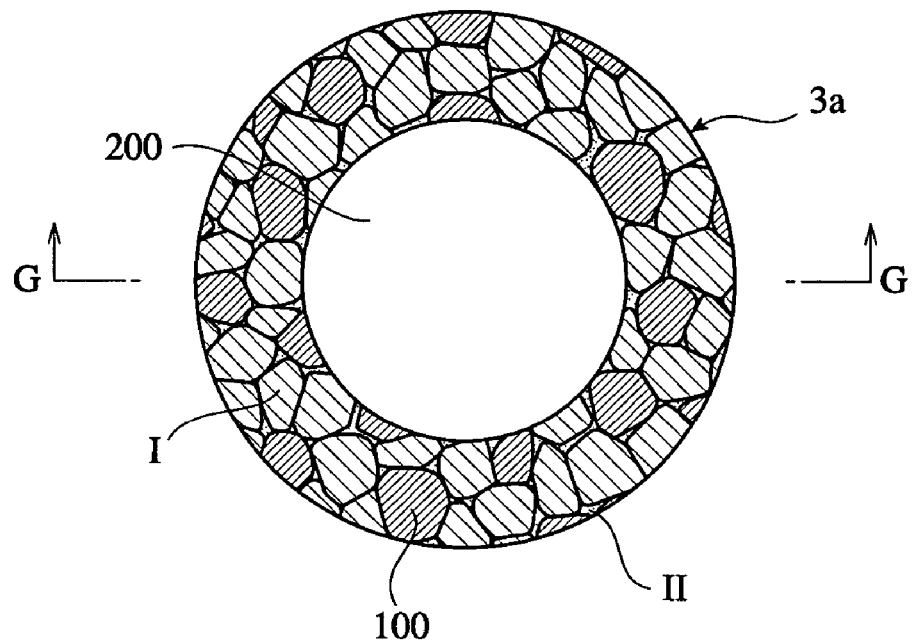
FIG. 8(a) is a top view showing a still further example of the calcium phosphate-synthetic resin-metal composite body of the present invention.
Figure 8B:
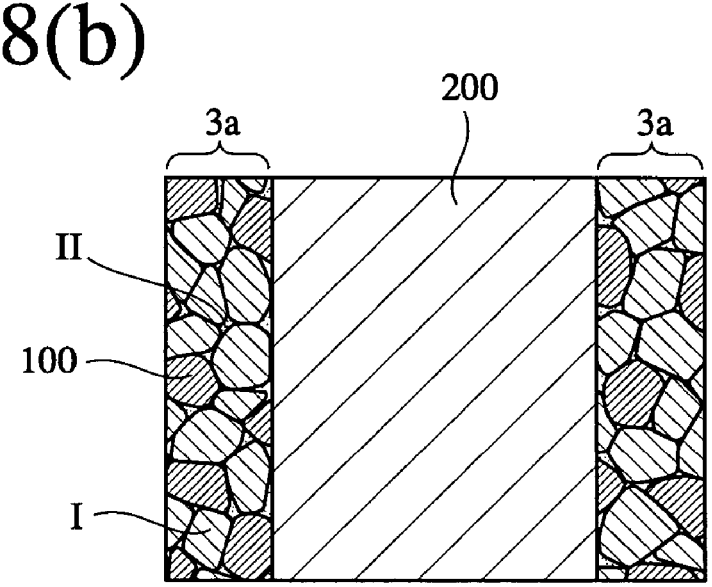
FIG. 8(b) is a vertical, cross-sectional view taken along the line G—G in FIG. 8(a)

The calcium phosphate-synthetic resin-metal composite body shown in FIGS. 8(a) and 8(b) has a double-layer structure comprising a cylindrical calcium phosphate-synthetic resin composite layer 3a (outer layer) and a columnar metal member 200 (inner layer) adhering to an inside surface of the cylindrical calcium phosphate-synthetic resin composite layer 3a. The composition of the calcium phosphate-synthetic resin composite layer 3a may be the same as in the example shown in FIG. 1.

Figure 9A:
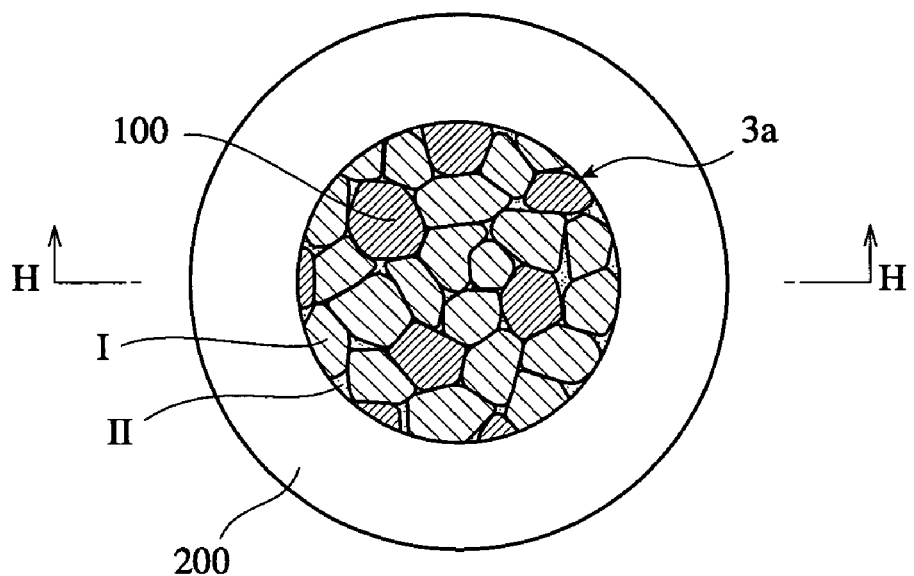
FIG. 9(a) is a top view showing a still further example of the calcium phosphate-synthetic resin-metal composite body of the present invention.
Figure 9B:
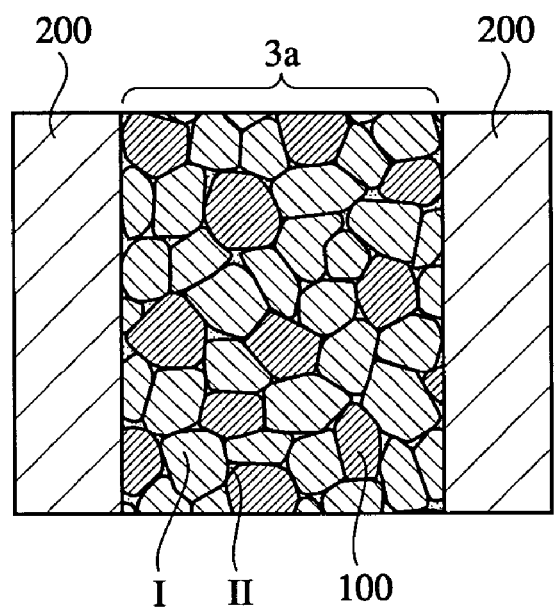
FIG. 9(b) is a vertical, cross-sectional view taken along the line H—H in FIG. 9(a)

The calcium phosphate-synthetic resin-metal composite body shown in FIG. 9(a) and 9(b) has a double-layer structure comprising an outer layer constituted by a cylindrical metal member 200 and an inner layer constituted by a calcium phosphate-synthetic resin composite layer 3a adhering to the metal member 200. The composition of the calcium phosphate-synthetic resin composite layer 3a may be the same as in the example shown in FIG. 1.

Figure 10A:
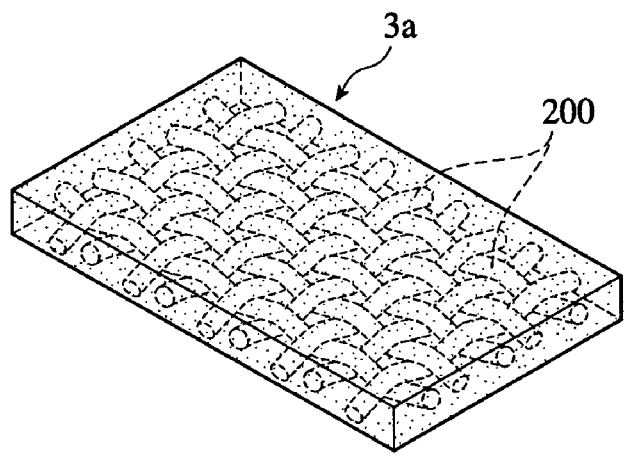
FIG. 10(a) is a perspective view showing a still further example of the calcium phosphate-synthetic resin-metal composite body of the present invention.
Figure 10B:
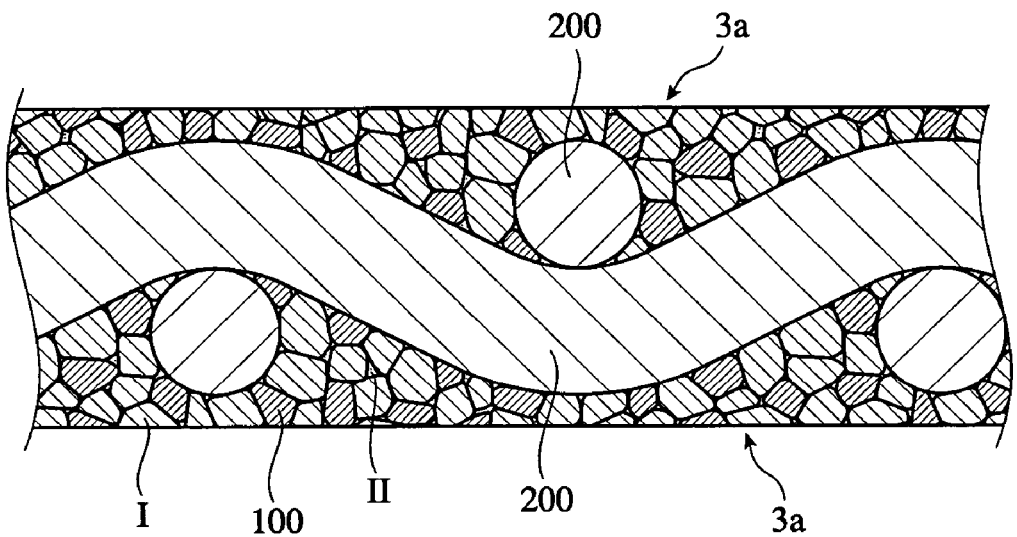
FIG. 10(b) is an enlarged cross-sectional view showing part of the example shown in FIG. 10(a)

The calcium phosphate-synthetic resin-metal composite body shown in FIGS. 10(a) and 10(b) having a plate shape comprises a mesh-shaped metal member 200, a calcium phosphate-synthetic resin composite layer 3a covering the entire surface of the metal member 200. The composition of the calcium phosphate-synthetic resin composite layer 3a may be the same as in the example shown in FIG. 1.

Figure 11A:
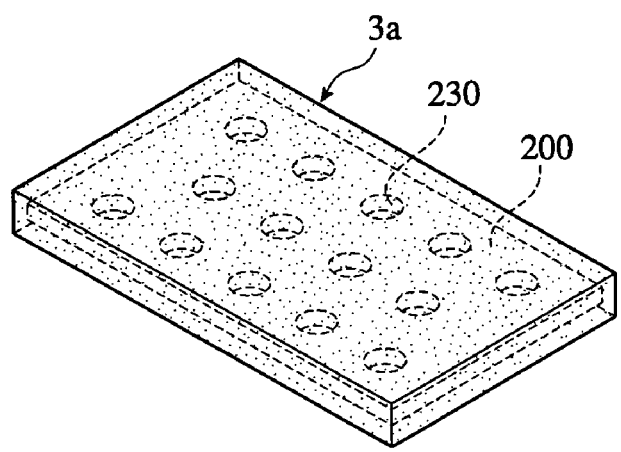
FIG. 11(a) is a perspective view showing a still further example of the calcium phosphate-synthetic resin-metal composite body of the present invention.
Figure 11B:
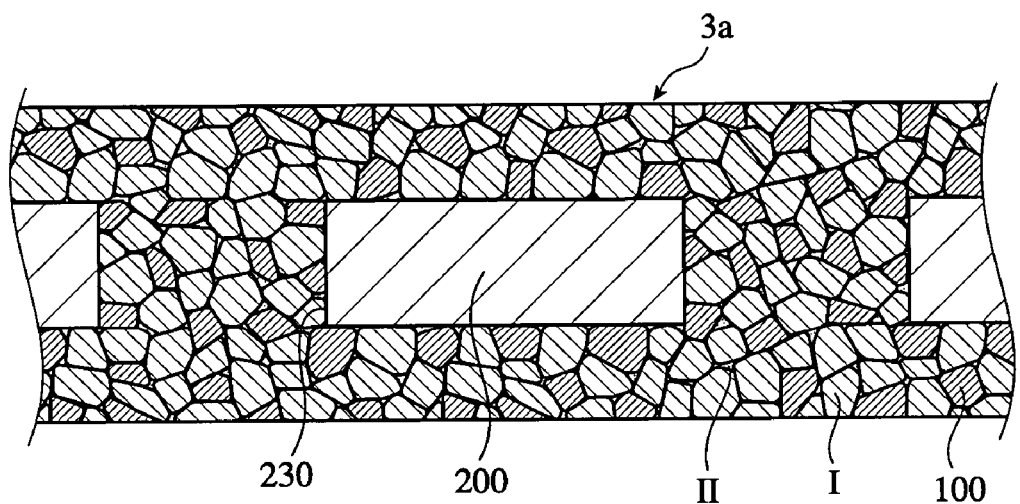
FIG. 11(b) is an enlarged cross-sectional view showing part of the example shown in FIG. 11(a)

The calcium phosphate-synthetic resin-metal composite body shown in FIGS. 11(a) and 11(b) comprises a plate-shaped metal member 200 and a calcium phosphate-synthetic resin composite layer 3a covering the entire surface of the metal member 200. The metal member 200 has a plurality of through-holes 230 arranged at a constant interval. As shown in FIG. 11(b), the calcium phosphate-synthetic resin composite layer 3a is filled in the through-holes 230, so that the calcium phosphate-synthetic resin composite layers 3a on both sides of the metal member 200 are connected with each other. Thus, the calcium phosphate-synthetic resin composite layer 3a does not easily peel off from the metal member 200. The composition of the calcium phosphate-synthetic resin composite layer 3a may be the same as in the example shown in FIG. 1.

FIGS. 13 and 14 show another example of the calcium phosphate-synthetic resin-metal composite body. This composite body has a cylindrical shape with a rectangular cross section, which is constituted by a metal member 200 shown in FIG. 12 and a calcium phosphate-synthetic resin composite layer 3a entirely covering the metal member 200.

Figure 14A:
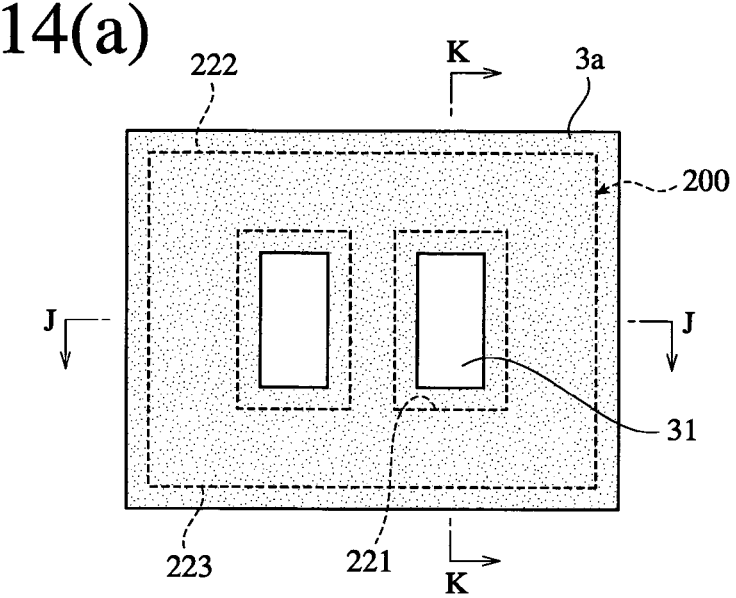
FIG. 14(a) is a side view showing the calcium phosphate-synthetic resin-metal composite body shown in FIG. 13.
Figure 14B:
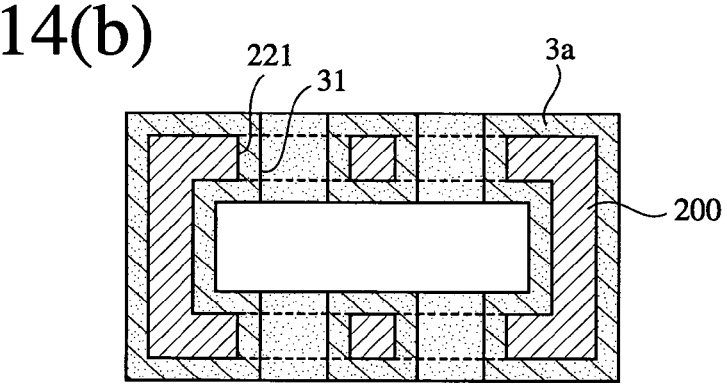
FIG. 14(b) is a cross-sectional view taken along the line J—J in FIG. 14(a)
Figure 14C:
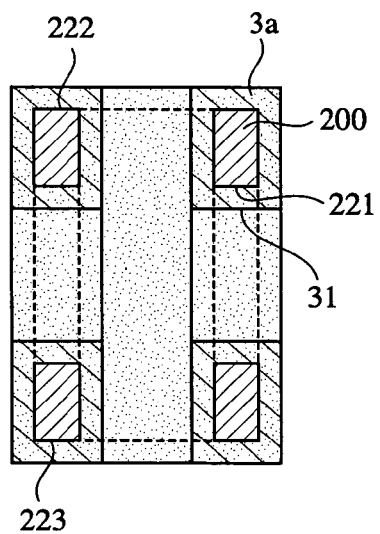
FIG. 14(c) is a cross-sectional view taken along the line K—K in FIG. 14(a)

FIG. 14(a) is a side view showing the calcium phosphate-synthetic resin-metal composite body of FIG. 13, FIG. 14(b) is a cross-sectional view taken along the line J—J in FIG. 14(a), and FIG. 14(c) is a cross-sectional view taken along the line K—K in FIG. 14(a). This calcium phosphate-synthetic resin-metal composite body has openings 31 in alignment with the windows 221 of the metal member 200. As shown in FIG. 14(b), the inside and outside surfaces of the metal member 200 and the side surfaces of the windows 221 are covered with the calcium phosphate-synthetic resin composite layer 3a. As shown in FIG. 14(c), because the upper surface 222 and the lower surface 223 of the metal member 200 are also covered with the calcium phosphate-synthetic resin composite layer 3a, the metal member 200 is not exposed at all. In other words, the cylindrical, windowed metal member 200 is completely embedded in the calcium phosphate-synthetic resin composite layer 3a.

Figure 15A:
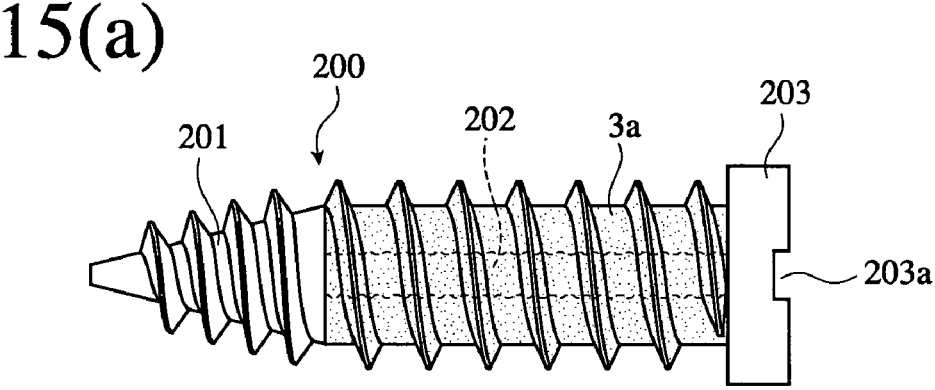
FIG. 15(a) is a side view showing a still further example of the calcium phosphate-synthetic resin-metal composite body of the present invention.
Figure 15B:
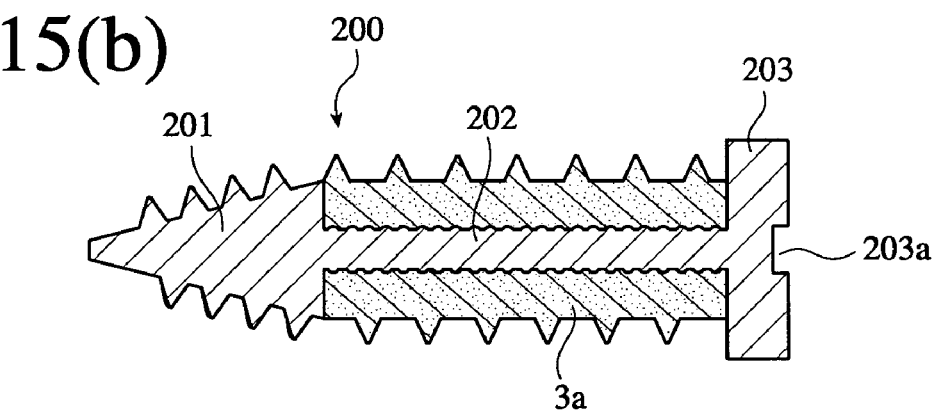
FIG. 15(b) is a cross-sectional view showing the example shown in FIG. 15(a)

FIG. 15(a) shows a side of a screw-shaped composite body, and FIG. 15(b) shows a vertical cross section thereof. This screw-shaped, calcium phosphate-synthetic resin-metal composite body comprises a metal screw 200 comprising a thread 201 having substantially conical shape, a trunk 202 having a smaller outer diameter than a base diameter of the conical thread 201, and a head 203 having a larger outer diameter than the base diameter of the conical thread 201; and a calcium phosphate-synthetic resin composite layer 3a covering the trunk 202. Each of the thread 201 and the calcium phosphate-synthetic resin composite layer 3a has a threaded surface. The trunk 202 preferably has an irregular surface to increase adhesion to the synthetic resin particles I and II. The screw head 203 has a plus- or minus-shaped groove 203a to rotate the screw-shaped composite body 200. As in the example shown in FIG. 1, the calcium phosphate-synthetic resin composite layer 3a is composed of a uniform mixture of the calcium phosphate particles 100 and the synthetic resin particles I and II. The calcium phosphate particles 100 are exposed on the surface of the calcium phosphate-synthetic resin composite layer 3a.

[2] Production of Calcium Phosphate-synthetic Resin-metal Composite Body (1) First Embodiment The present invention utilizes a pressing/heating method to produce the calcium phosphate-synthetic resin-metal composite body. The calcium phosphate-synthetic resin-metal composite body may or may not contain a calcium phosphate block. Explanation will be made below mainly on the production of a composite body containing a calcium phosphate block. The composite body containing no calcium phosphate block can also be obtained by a similar pressing/heating method.

(a) Production of Calcium Phosphate Block

The calcium phosphate block may be produced by common methods, but it is preferably produced by the methods described in JP 2-167868 A and JP 8-48583 A, foaming methods, and methods of adding thermally decomposable beads. The disclosures of JP 2-167868 A and JP 8-48583 A are incorporated by reference herein in their entireties. The method for producing a calcium phosphate-synthetic resin composite body, which is described in JP 2-167868 A, is a method (I) where a slurry or a fluid gel containing calcium phosphate compound powder and a polymer material is foamed and then thickened or gelated, and the resultant foamed body is sintered if necessary. The method for producing a calcium phosphate-synthetic resin composite body, which is described in JP 8-48583 A, is a method (II) where polysaccharide particles and ceramic particles are mixed and compressed to form a green compact, which is sintered.

(b) Production of Calcium Phosphate-synthetic Resin-metal Composite Body (I) Pressing/Heating Apparatus Preferable pressing/heating methods for producing the calcium phosphate-synthetic resin-metal composite body include a method where a metal member, a mixture comprising the calcium phosphate particles and the synthetic resin particles I and II, and a calcium phosphate block are charged between a pair of dies connected to a heat source, which are heated while applying pressure. The pressing/heating is preferably carried out in vacuum, or in an atmosphere of an inert gas such as $N_2$, He and Ar.

Figure 16:
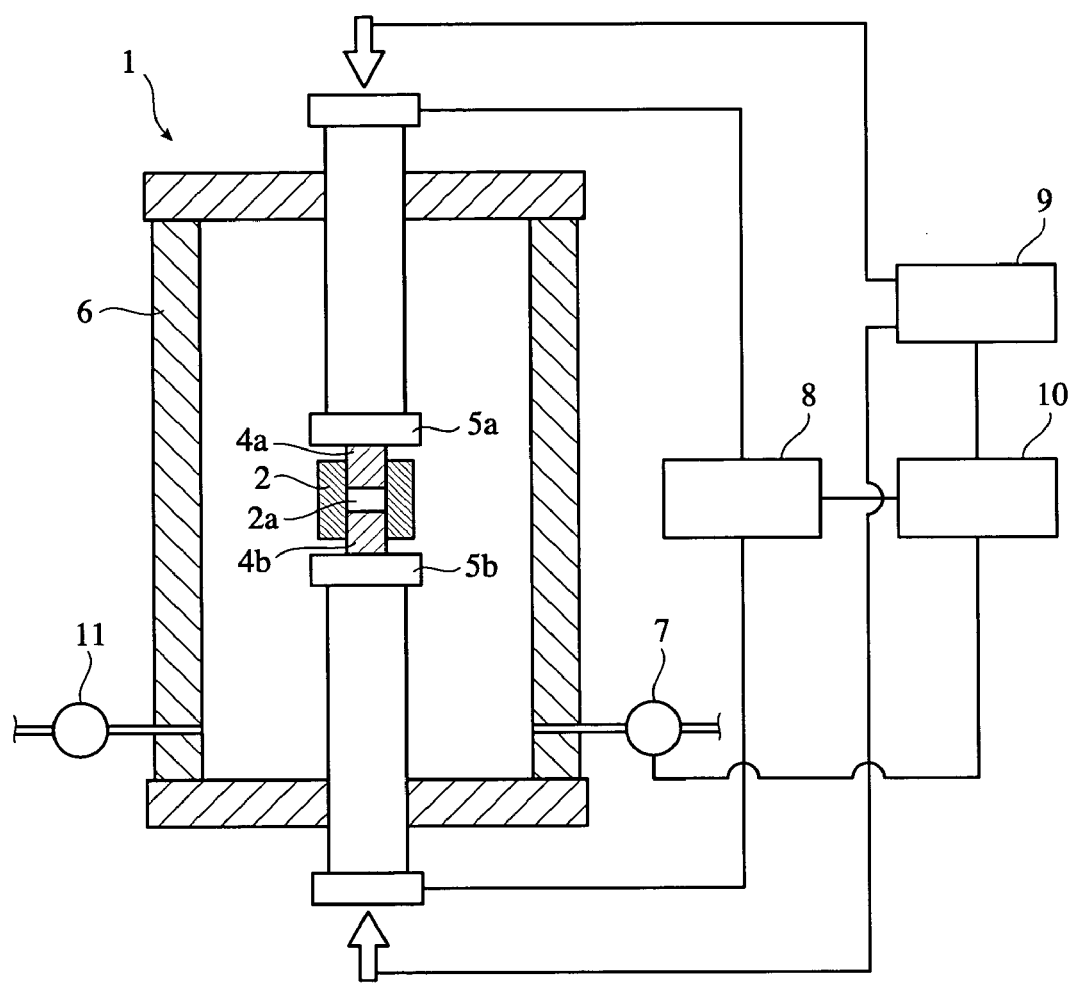
FIG. 16 is a schematic view showing the structure of the vacuum pressing/heating apparatus.
Figure 17:
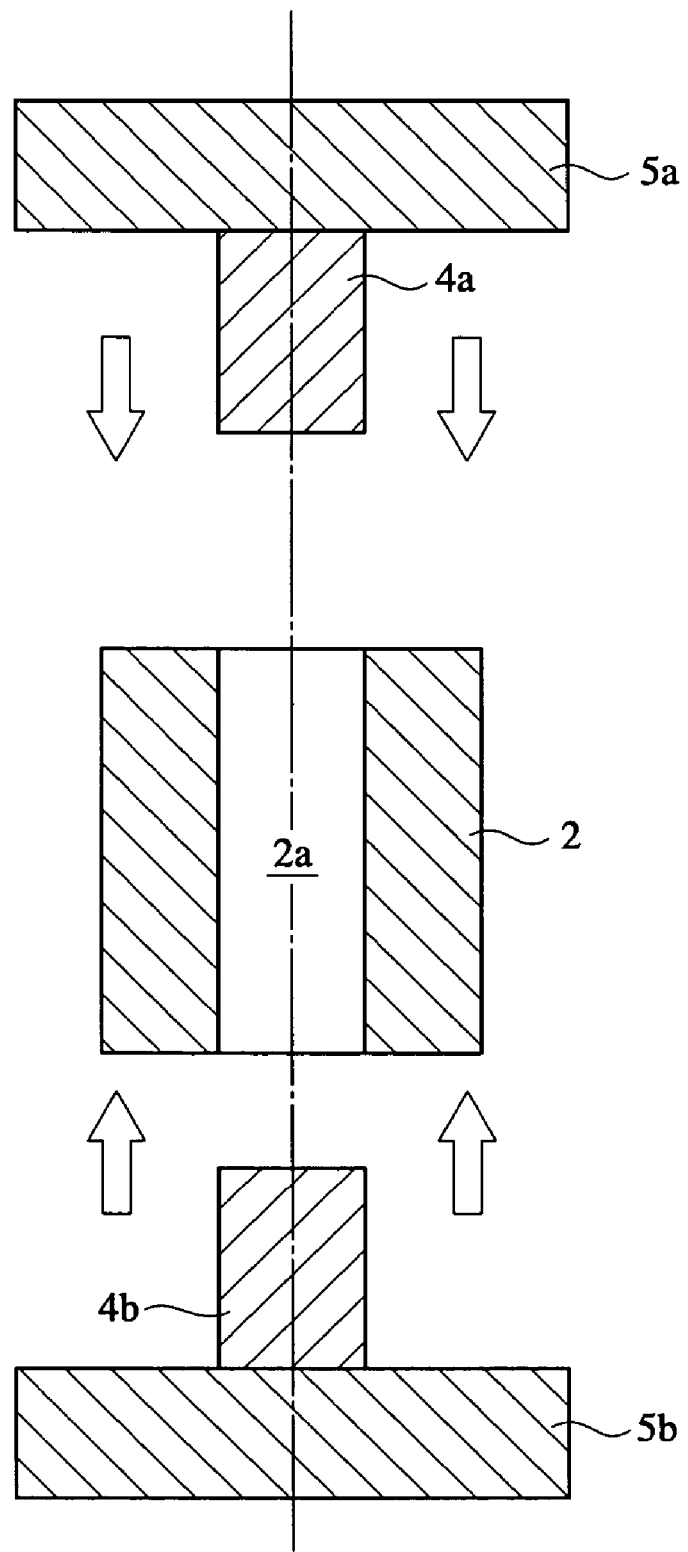
FIG. 17 is an exploded cross-sectional view showing the molding die of the vacuum pressing/heating apparatus shown in FIG. 16.
Figure 18:
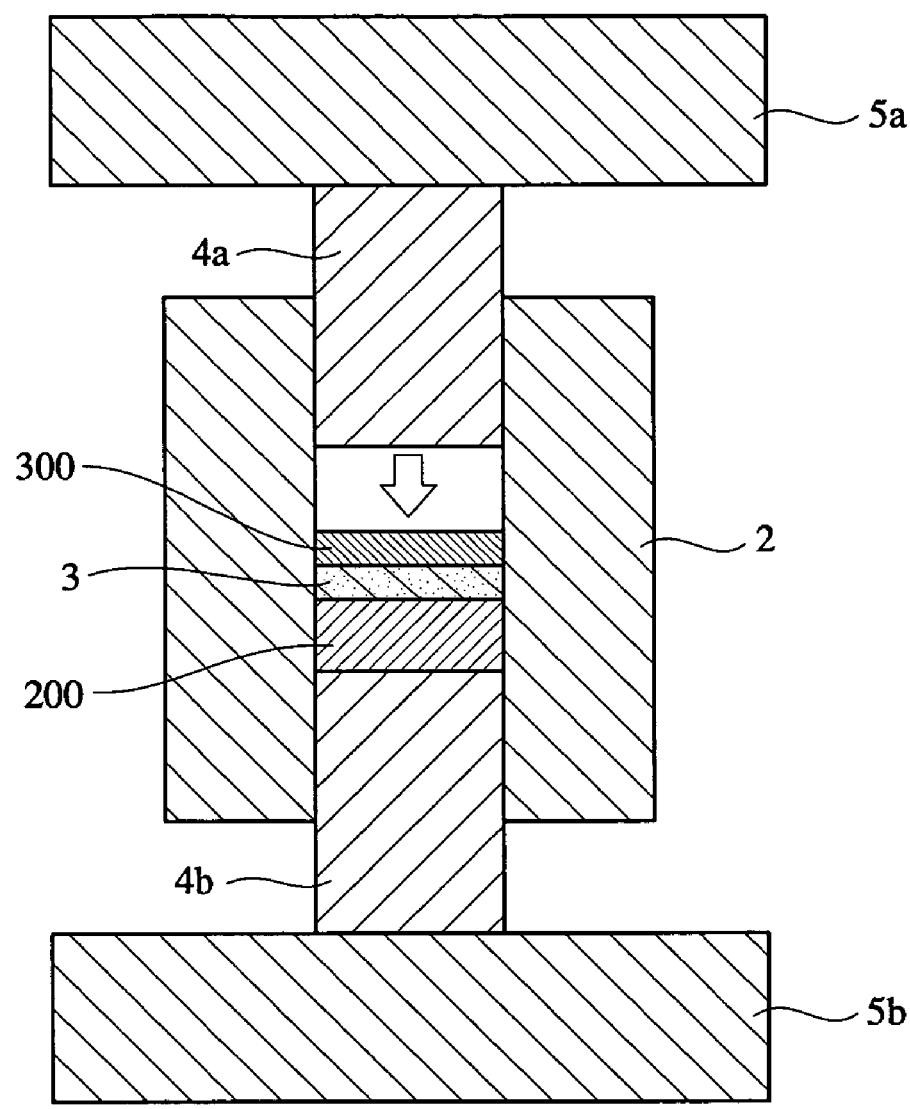
FIG. 18 is a vertical cross-sectional view showing a state in which a metal member, a mixture and a calcium phosphate block are charged into a cavity of a molding die shown in FIG. 17.

FIGS. 16 to 18 show an example of apparatuses for carrying out a pressing/heating treatment in vacuum or in an inert gas atmosphere. In FIG. 16, the pressing/heating apparatus 1 has a vacuum chamber 6 provided with a vacuum pump 7, a stationary die member 2 disposed therein, a pair of punches 4a and 4b for pressing a metal member, a mixture of the calcium phosphate particles and the synthetic resin particles I and II, and a calcium phosphate block introduced into a cavity 2a of the stationary die member 2 while heating, and rams 5a and 5b for driving the punches 4a and 4b. A thermocouple (not shown) for measuring the heating treatment temperature may be disposed in the stationary die member 2. A gas pump 11 is connected to a gas inlet member and a gas container (not shown).

Each ram 5a and 5b is driven by a press-driving mechanism 9 to press the mixture 3 while heating each punch 4a and 4b, with electric power received from a power supply 8 connected via a terminal (not shown). A control means 10 is connected to the press-driving mechanism 9, the power supply 8, the vacuum pump 7 and the thermocouple to control a heating temperature in the stationary die member 2 and a degree of vacuum in the vacuum chamber 6.

As is shown in FIG. 17, the stationary die member 2 has an annular structure having a cavity 2a having a circular, oval or rectangular cross section. Each punch 4a and 4b has a slightly smaller cross section than the cavity 2a such that it can move up and down in the cavity 2a of the stationary die member 2. The punches 4a and 4b are secured to the rams 5a and 5b, respectively.

(II) Charging

The metal member, a mixture comprising the calcium phosphate particles and the synthetic resin particles I and II, and the calcium phosphate block are charged into the cavity 2a of the stationary die member 2 such that the calcium phosphate particles and a calcium phosphate block are exposed on at least part of the surface of the resultant composite body, and that the synthetic resin particles I and II surround the calcium phosphate particles.

The mass ratio of the calcium phosphate particles to the synthetic resin particles is preferably 1/9 to 8/2. When the mass ratio of the calcium phosphate particles is more than 8/2, the calcium phosphate particles are not completely surrounded by the synthetic resin particles, resulting in easy detachment of the calcium phosphate particles. On the other hand, when the mass ratio of the calcium phosphate particles is less than 1/9, the ratio of calcium phosphate in the composite body is too low, resulting in low biocompatibility.

Figure 19A:
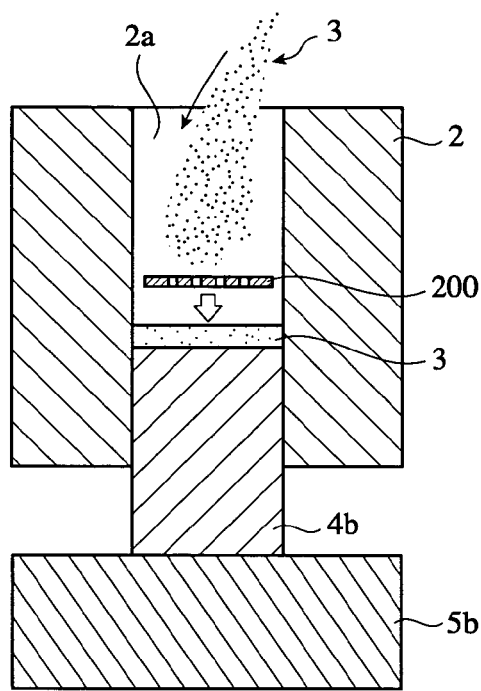
FIG. 19(a) is a cross-sectional view showing the step of producing a plate-shaped calcium phosphate-synthetic resin-metal composite body, in which a cylindrical metal member and a mixture are charged into a cavity of the molding die of the vacuum pressing/heating apparatus.
Figure 19B:
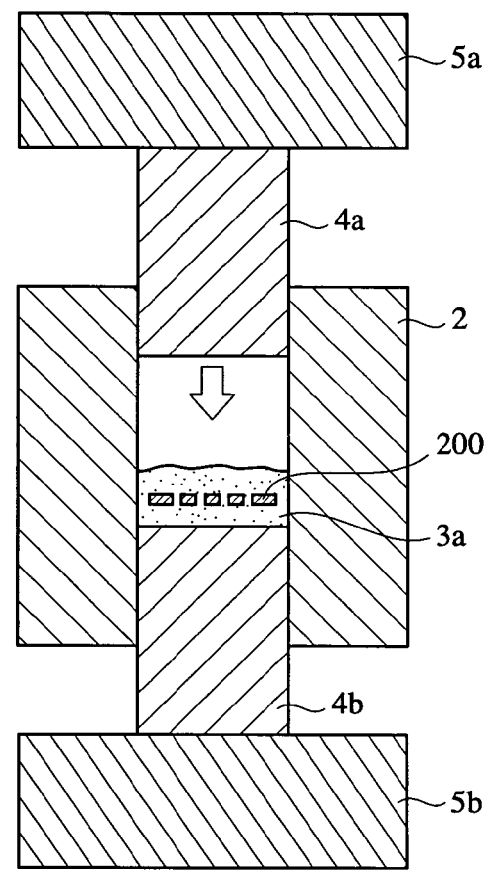
FIG. 19(b) is a cross-sectional view showing the step of producing a plate-shaped calcium phosphate-synthetic resin-metal composite body, in which the metal member and the mixture charged into the molding die cavity are heated while pressing.

For instance, when the calcium phosphate-synthetic resin-metal composite body shown in FIGS. 1(a) and (b) is produced, the metal member 200, the mixture 3a of the calcium phosphate particles and the synthetic resin particles I and II, and the calcium phosphate block 300 are charged into the cavity 2a of the stationary die member 2 shown in FIG. 16 in this order as is shown in FIG. 18. Alternatively, when the calcium phosphate-synthetic resin-metal composite body shown in FIG. 10 or 11 is produced, a mixture 3 of the calcium phosphate particles and the synthetic resin particles I and II are charged into the cavity 2a to the height of about 10 to 10 mm, and a mesh- or plate-shaped metal member 200 is then put into the cavity 2a, as shown in FIG. 19(a). The mixture 3 is further added on the metal member 200 to the height of about 5 to 10 mm, as shown in FIG. 19(b). The mixture 3 enters into the meshes or through-holes 230 of the metal member 200. Thus, the step of charging materials into the die cavity 2a may be conducted depending on the structure of a calcium phosphate-synthetic resin-metal composite body to be produced.

(III) Pressing/Heating Treatment

In the case of the calcium phosphate-synthetic resin-metal composite body shown in FIGS. 1(a) and (b), after the metal member 200, the mixture 3 and the calcium phosphate block 300 are charged into the cavity 2a in this order as is shown in FIG. 18, and the vacuum chamber 6 is sealed and evacuated by the vacuum pump 7 to a degree of vacuum of about 1 Pa. Thereafter, an inert gas such as $N_2$, He or Ar may be introduced to carry out the pressing/heating treatment in a low-concentration oxygen condition, thereby preventing the oxidative degradation of synthetic resin particles.

When the press-driving mechanism 9 is operated by the control means 10, at least one of the rams 5a and 5b moves in a direction to approach one another, so that the punches 4a and 4b secured thereto press the mixture 3. The pressing power of the punches 4a and 4b is preferably 0.5 to 50 MPa, and more preferably 1.0 to 20 MPa. When the pressing power is less than 0.5 MPa, sufficient adhesion is not achieved between the synthetic resin particles and the metal member, the synthetic resin particles and the calcium phosphate particles, and the synthetic resin particles and the calcium phosphate block, resulting in easy detachment of the metal member, the calcium phosphate particles and the calcium phosphate block from the resultant composite body. Even if it were more than 50 MPa, however, correspondingly improved shape retention would not be obtained, rather resulting in problems such as the collapse of the calcium phosphate particles and the calcium phosphate block.

The punches 4a and 4b are heated by the power supply 8 to heat the mixture 3 under pressure. The mixture 3 is preferably heated according to a predetermined temperature elevation program. In that case, the temperature of the mixture 3 is detected by a thermocouple (not shown) disposed in the stationary die member 2, and an output of the thermocouple is sent to the control means 10. The control means 10 produces a signal for temperature elevation according to the temperature elevation program on the basis of input temperature data, and sends it to the power supply 8. The power supply 8 supplies appropriate current to the rams 5a and 5b according to a command from the control means 10.

The heating temperature is preferably 130° C. to 300° C., and more preferably 150° C. to 250° C. When the heating temperature is lower than 130° C., sufficient adhesion is not achieved between the synthetic resin particles and the metal member, the synthetic resin particles and the calcium phosphate particles, and the synthetic resin particles and the calcium phosphate block, resulting in easy detachment of the metal member, the calcium phosphate particles and the calcium phosphate block from the composite body. The heating temperature higher than 300° C. is not preferable, because the synthetic resin particles cannot retain their shapes, sometimes resulting in integration by melting.

The heating time (time period in which the heating temperature is kept) is preferably 1 to 30 minutes. When the heating time is shorter than one minute, sufficient adhesion is not achieved between the synthetic resin particles and the metal member, the synthetic resin particles and the calcium phosphate particles, and the synthetic resin particles and the calcium phosphate block. The heating time longer than 30 minutes is not preferable, because it would not provide improved adhesion. A more preferable heating time is 3 to 10 minutes.

After the pressing/heating treatment, the calcium phosphate-synthetic resin-metal composite body is cooled to room temperature, and removed from the stationary die member. When the calcium phosphate particles are not exposed sufficiently on the surface of the composite body, the surface may be ground.

(2) Second Embodiment

The production of the cylindrical calcium phosphate-synthetic resin-metal composite body shown in FIGS. 13 and 14 according to the second embodiment is the same as that according to the first embodiment, except for charging a mixture 3 of calcium phosphate particles and synthetic resin particles I and II and a metal member 200 into the cavity 2a of the stationary die member 2. Thus, only different part of the processes will be explained below.

Figure 20A:
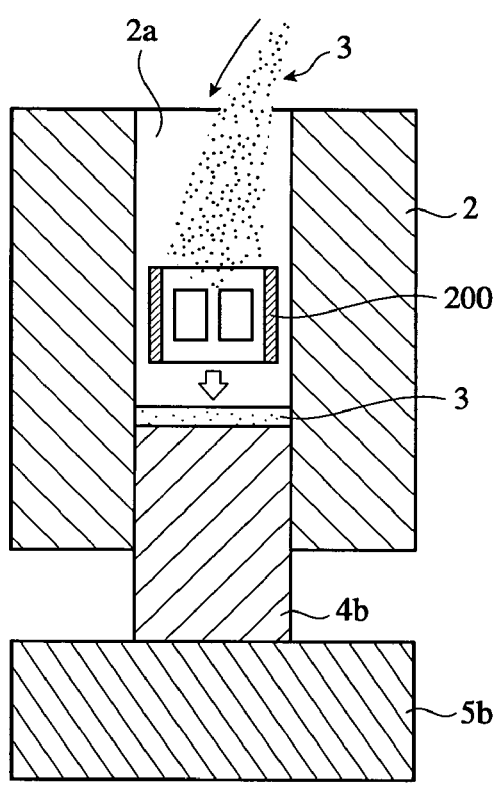
FIG. 20(a) is a cross-sectional view showing the step of producing a metal member-embedded composite body, in which a cylindrical metal member and a mixture are charged into a cavity of the molding die of the vacuum pressing/heating apparatus.

As shown in FIG. 20(a), a mixture 3 of the calcium phosphate particles and the synthetic resin particles I and II is charged into the cavity 2a of the stationary die member 2, such that the mixture 3 lies uniformly on a bottom surface of the cavity 2a. After the mixture 3 becomes as high as about 5 to 10 mm, the metal member 200 is introduced into the cavity 2a, and a mixture 3 is further introduced into the cavity 2a such that the mixture 3 exists inside and outside the metal member 200. Because the mixture 3 is charged outside the metal member 200, too, the inner size of the cavity 2a is about 3 to 10 mm larger than the outer size of the metal member 200.

Figure 20B:
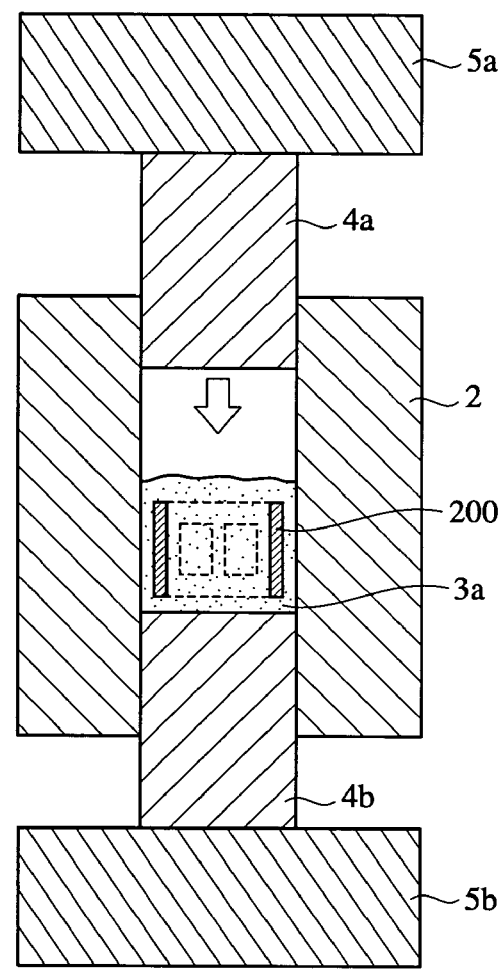
FIG. 20(b) is a cross-sectional view showing the step of producing a metal member-embedded composite body, in which the metal member and the mixture charged into the molding die cavity are heated while pressing.
Figure 21:
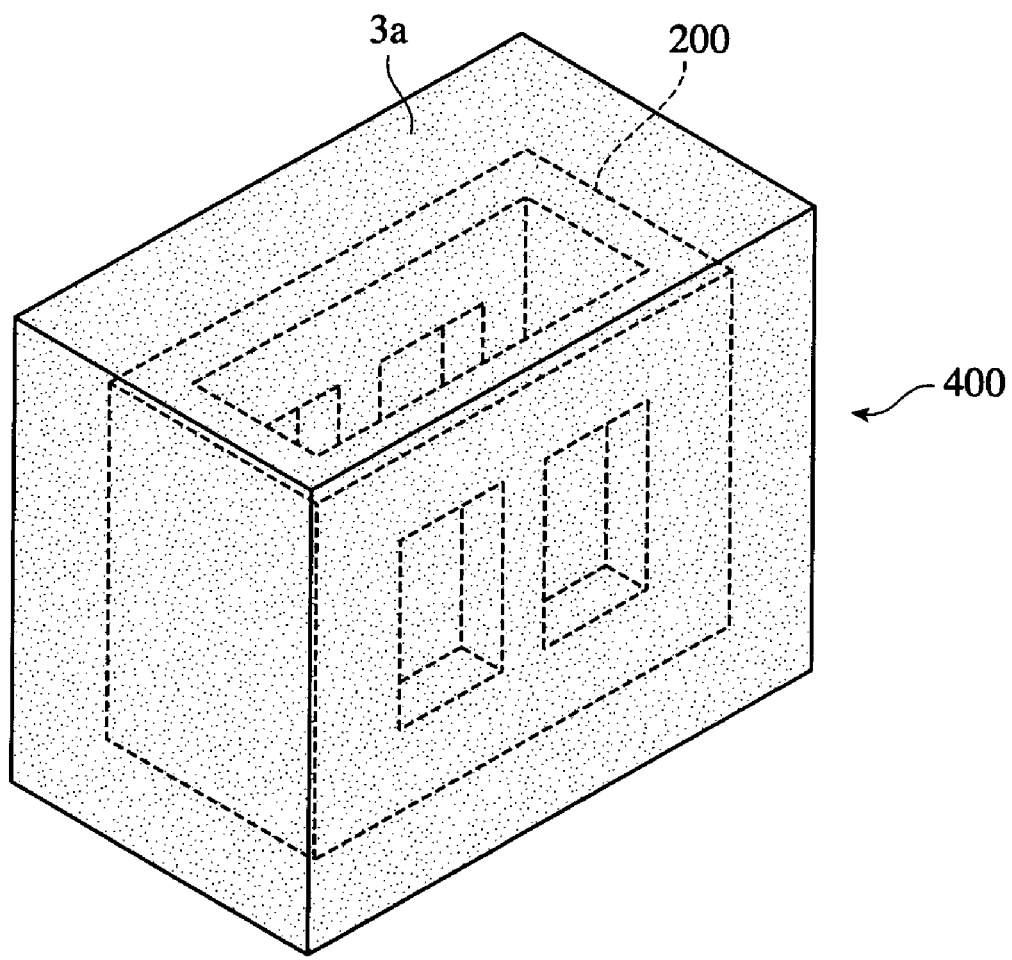
FIG. 21 is a perspective view showing the cylindrical metal member-embedded composite body obtained by the process shown in FIG. 20.

As shown in FIG. 20(b), with the mixture 3 lying on the metal member 200 at a height of about 5 to 10 mm, the content in the cavity 2a is pressed while heating. The pressing/heating treatment provides a composite body 400 constituted by the metal member 200 and a calcium phosphate-synthetic resin composite layer 3a covering the entire surface of the metal member 200, as shown in FIGS. 21 and 22. This composite body 400 is left to cool to room temperature and then taken out from the molding die cavity. This composite body is a solid body comprising the metal member 200 embedded in the calcium phosphate-synthetic resin composite body, which may be called "metal member-embedded composite body."

Figure 22A:
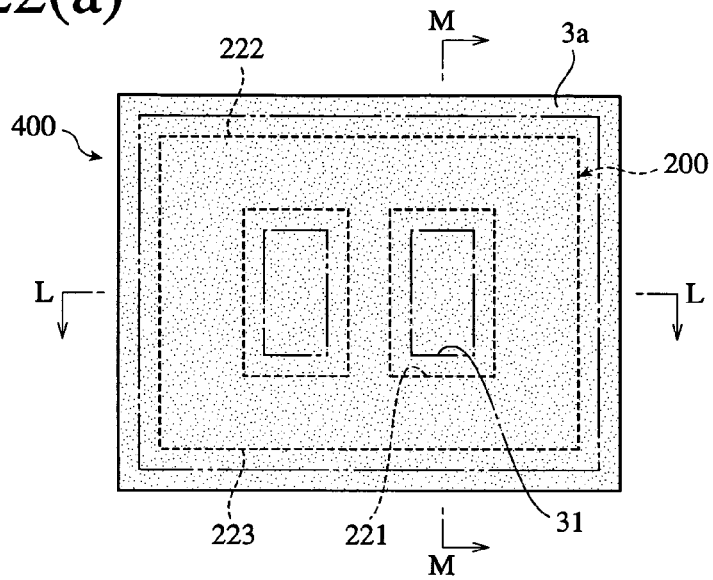
FIG. 22(a) is a side view showing the cylindrical metal member-embedded composite body shown in FIG. 21.
Figure 22B:
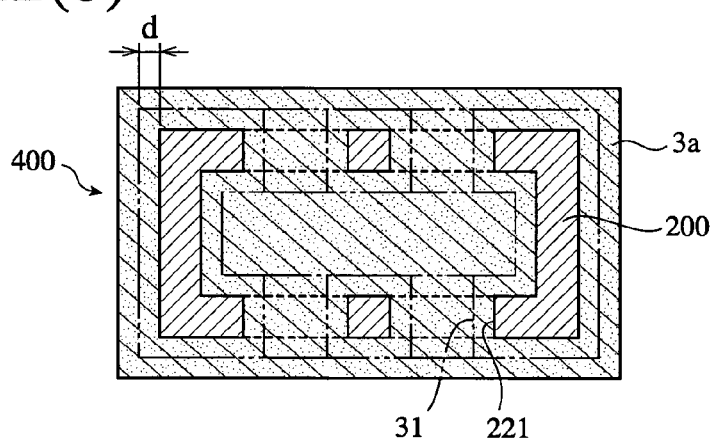
FIG. 22(b) is a cross-sectional view taken along the line L—L in FIG. 22(a)
Figure 22C:
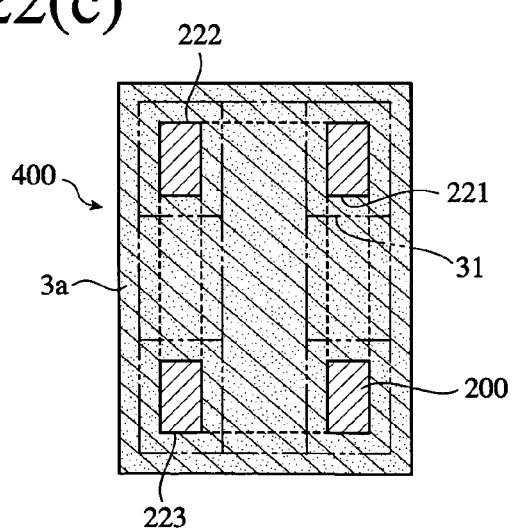
FIG. 22(c) is a cross-sectional view taken along the line M—M in FIG. 22(a)

FIG. 22(a) is a side view showing a cylindrical metal member-embedded composite body 400, FIG. 22(b) is a cross-sectional view taken along the line L—L in FIG. 22(a), and FIG. 22(c) is a cross-sectional view taken along the line M—M in FIG. 22(a). The calcium phosphate-synthetic resin composite body inside the metal member 200 is cut away from the solid metal member-embedded composite body to make it cylindrical, and the calcium phosphate-synthetic resin composite body is cut at positions corresponding to the windows of the metal member 200 to provide the cylindrical metal member-embedded composite body with openings 31. The calcium phosphate-synthetic resin composite body is cut away such that a calcium phosphate-synthetic resin composite layer 3a remains preferably in a thickness d of 0.5 to 2 mm on the inside and outside surfaces and the upper and lower end surfaces 222, 223 of the metal member 200. The cylindrical, windowed calcium phosphate-synthetic resin-metal composite body thus obtained comprises a cylindrical, windowed metal member 200 and a calcium phosphate-synthetic resin composite layer 3a formed on the entire surface of the metal member 200. The calcium phosphate-synthetic resin composite layer 3a is shown by the broken lines in FIGS. 22(b) and 22(c).

(3) Third Embodiment

Figure 23:
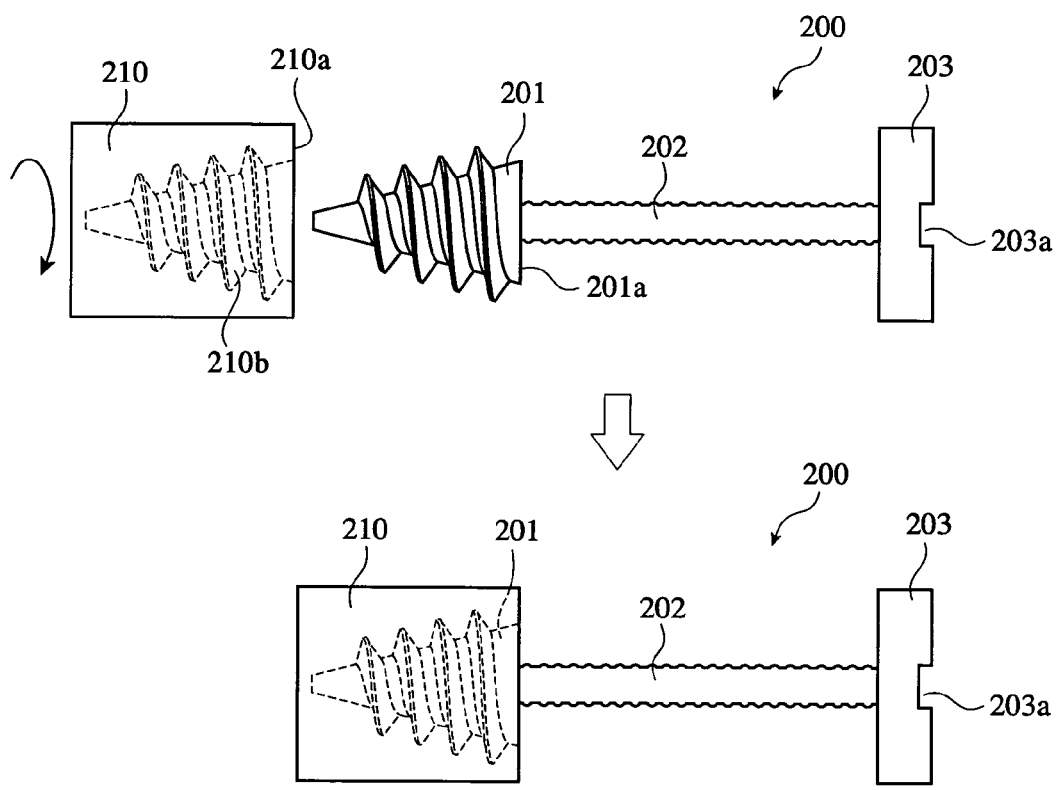
FIG. 23 is a cross-sectional view showing the step for putting a cap on a metal screw to produce the composite body shown in FIG. 15.

Because of the special shape of the composite body shown in FIGS. 15(a) and (b), it is produced, for instance, as follows. To protect a thread 201 of a metal screw 200 during the molding process, the thread 201 puts on a cylindrical metal cap 210 having a threaded hole 210b complementary to the thread 201, as shown in FIG. 23. The depth of the threaded hole 210b of the metal cap 210 is determined such that an opened surface 210a of the metal cap 210 is aligned with the base surface 201a of the thread 201 are substantially when the thread 201 completely engages the threaded hole 210b. Because the metal cap 210 is removed from the metal screw 200 after the molding, at least one of the thread 201 and the threaded hole 210b is preferably coated with a parting agent such as silicone for easy detachment.

Figure 24:
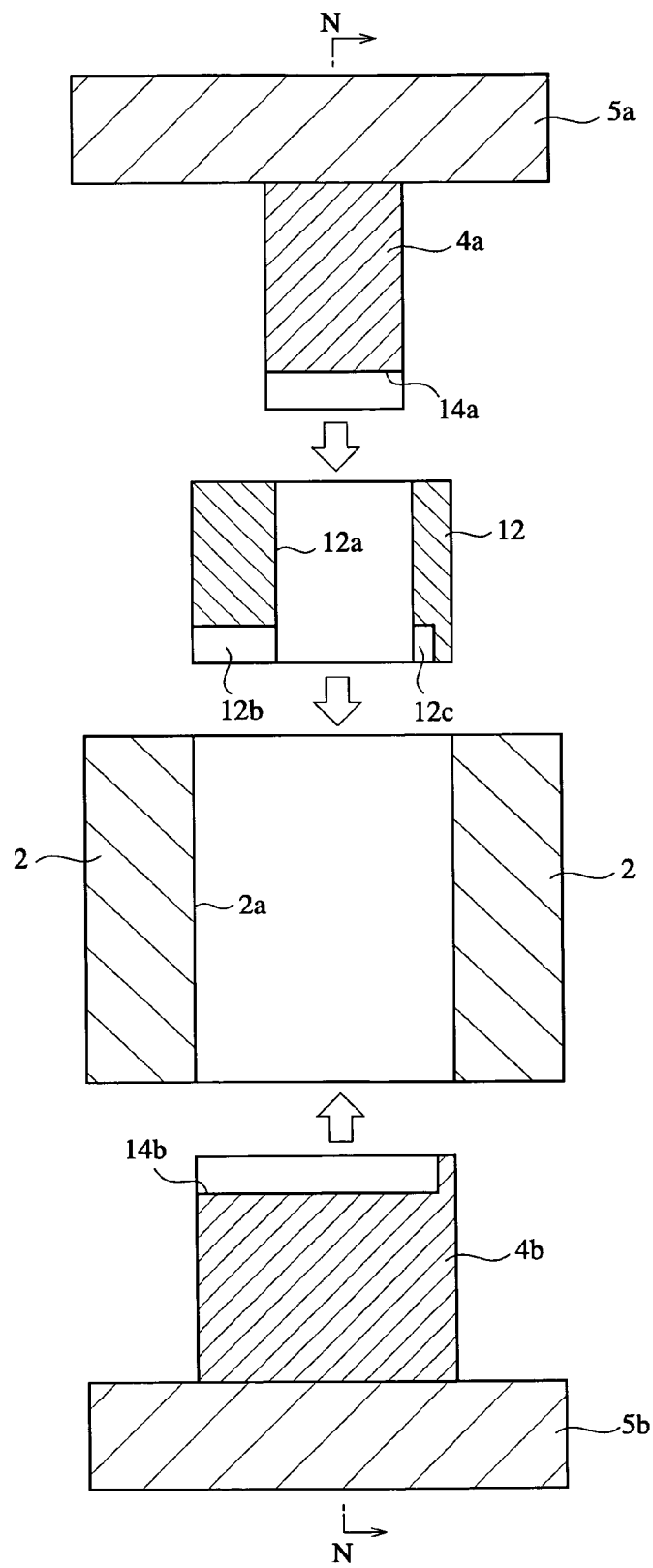
FIG. 24 is a vertical cross-sectional view showing the molding die of the vacuum pressing/heating apparatus for producing the screw-shaped composite body shown in FIG. 15.
Figure 25:
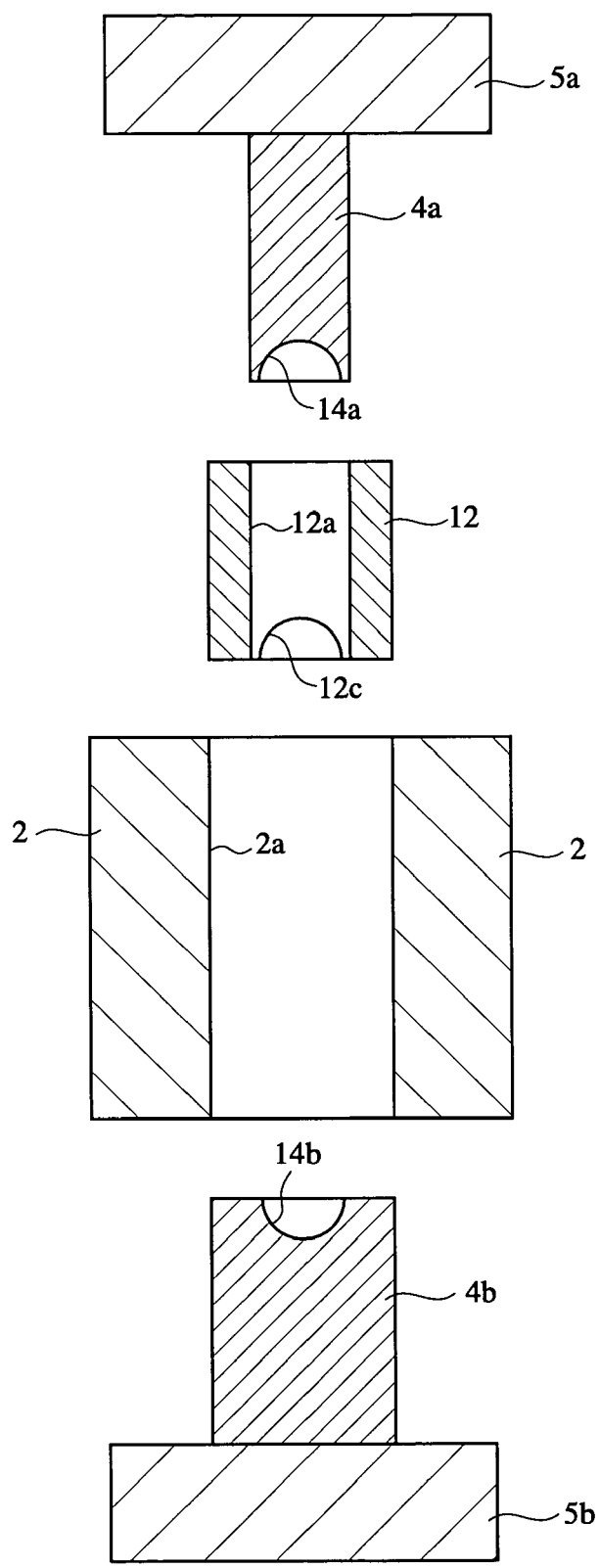
FIG. 25 is a cross-sectional view taken along the line N—N in FIG. 24.

FIGS. 24 and 25 show an example of the pressing/heating apparatus for producing the screw-shaped composite body shown in FIG. 15. FIG. 24 is a vertical cross-sectional view showing the molding die in an open state, and FIG. 25 is a cross-sectional view taken along the line N-N in FIG. 24. This molding apparatus comprises a stationary die member 2 having a vertically penetrating cavity 2a with a rectangular cross section, a lower punch 4b entering into the cavity 2a of the stationary die member 2 from below, a protection die 12 entering into the cavity 2a of the stationary die member 2 from above to abut the lower punch 4b, and an upper punch 4a entering into the cavity 12a of the protection die 12 from above to abut the lower punch 4b. Driving rams 5a, 5b are attached to the punches 4a, 4b, respectively.

The lower punch 4b has a semicylindrical cavity 14b for receiving the metal screw 200 on a top surface. The semicylindrical cavity 14b is open at one end and closed at the other end in a longitudinal direction. The semicylindrical cavity 14b is positioned such that it is exposed to the cavity 2a of the stationary die member 2. The upper punch 4a has a semicylindrical cavity 14a having the same shape as that of the semicylindrical cavity 14b of the lower punch 4b at a position in alignment with the semicylindrical cavity 14b. Both semicylindrical cavities 14a and 14b have a shape substantially complementary to the cap 210 and the head 203 of the metal screw 200, respectively.

Figure 26A:
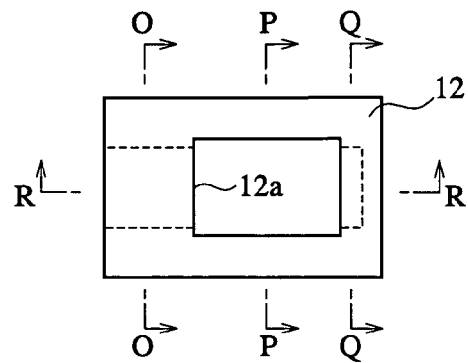
FIG. 26(a) is a top view showing a protection die used in the vacuum pressing/heating apparatus shown in FIG. 24.
Figure 26B:
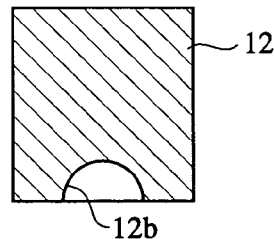
FIG. 26(b) is a cross-sectional view taken along the line O—O in FIG. 26(a)
Figure 26C:
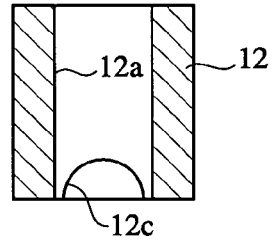
FIG. 26(c) is a cross-sectional view taken along the line P—P in FIG. 26(a)
Figure 26D:
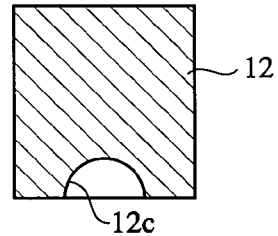
FIG. 26(d) is a cross-sectional view taken along the line Q—Q in FIG. 26(a)
Figure 26E:
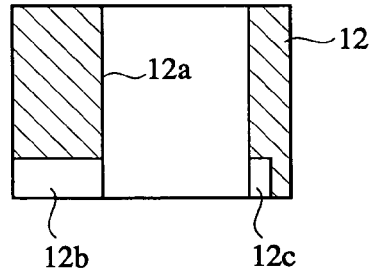
FIG. 26(e) is a cross-sectional view taken along the line R—R in FIG. 26(a)

FIGS. 26(a) to 26(e) shows the protection die 12; FIG. 26(a) is a top view of the protection die 12, FIG. 26(b) is a cross-sectional view taken along the line O—O in FIG. 26(a), FIG. 26(c) is a cross-sectional view taken along the line P—P in FIG. 26(a), FIG. 26(d) is a cross-sectional view taken along the line Q—Q in FIG. 26(a), and FIG. 26(e) is a cross-sectional view taken along the line R—R in FIG. 26(a). The protection die 12 has a rectangular shape with such a size that it is accurately received in the cavity 2a of the stationary die member 2. The protection die 12 comprises a cavity 12a vertically penetrating therethrough and having the same rectangular shape as the outer shape of the upper punch 4a as shown in FIG. 26(a); and semicylindrical cavities 12b, 12c extending in the longitudinal direction of the cavity 12a as shown in FIGS. 26(b) to 26(e). The semicylindrical cavities 12b and 12c have complementary shapes to the metal screw 200 provided with the cap 210. The longitudinally aligned semicylindrical cavities 12b and 12c receive the metal screw 200 at an accurate position in cooperation with the semicylindrical cavity 14b of the lower punch 4b. The semicylindrical cavity 12c exactly has a length for accommodating the screw head 203 (length equal to the thickness of the screw head 203), functioning as a protector for the screw head 203 when the metal screw 200 is set in the die cavity 2a.

Figure 27:
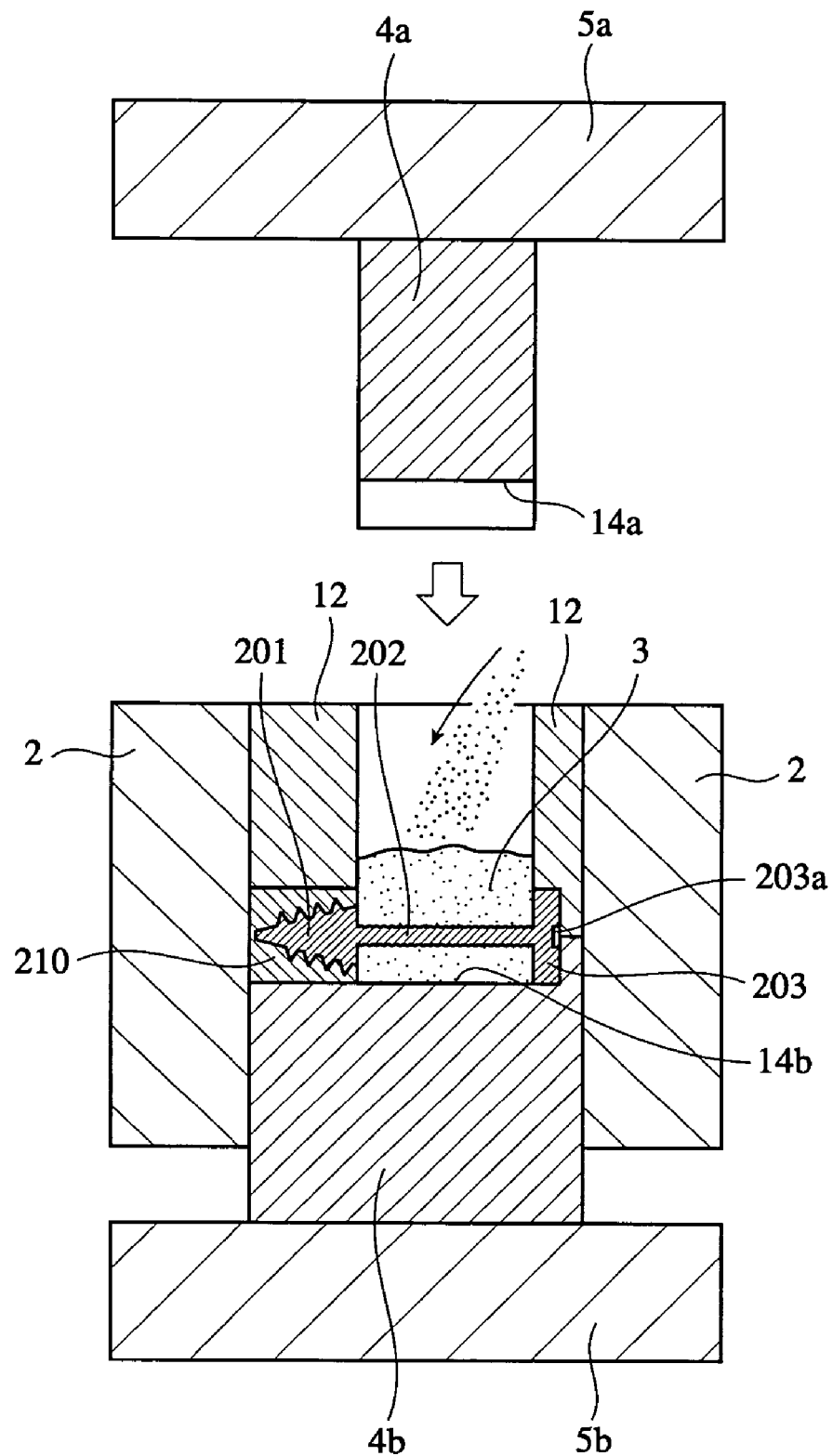
FIG. 27 is a vertical cross-sectional view showing a state in which the mixture is charged into the molding die of the vacuum pressing/heating apparatus with the capped screw placed therein.

Described below is an example of the production of the screw-shaped composite body shown in FIG. 15 by using the apparatus having the structure shown in FIGS. 24 to 26. First, as shown in FIG. 27, with the metal screw 200 provided with the cap 210 placed in the semicylindrical cavity 14b of the lower punch 4b, the lower punch 4b is moved upward and is stopped around a center of the cavity 2a of the stationary die member 2. The protection die 12 is then moved down in this state, until the semicylindrical cavities 12b and 12c of the protection die 12 mate the semicylindrical cavity 14b of the lower punch 4b to provide a cylindrical cavity, in which the cap 210 and the screw head 203 are fixed.

Figure 28A:
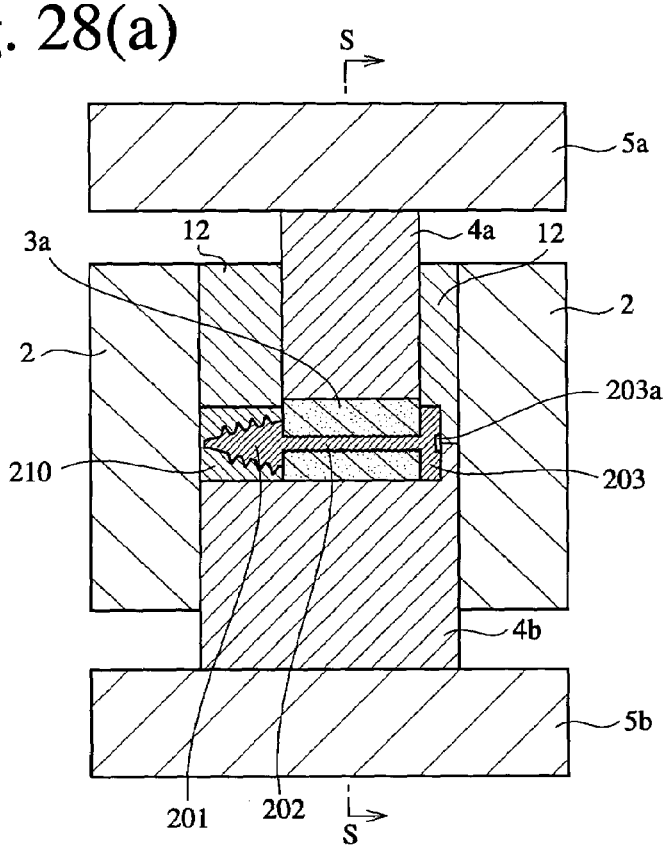
FIG. 28(a) is a vertical cross-sectional view showing a state in which the mixture is heated while pressing with the capped screw fixed in the molding die.
Figure 28B:
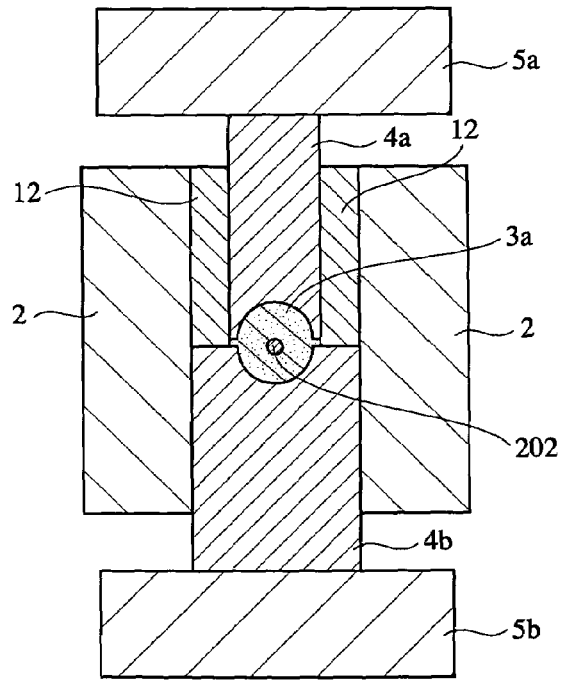
FIG. 28(b) is a cross-sectional view taken along the line S—S in FIG. 28(a)

In this state, the mixture 3 of the calcium phosphate particles and the synthetic resin particles I and II is charged into the cavity 14b of the lower punch 4b and the cavity 12a of the protection die 12. As shown in FIG. 28(a), the upper punch 4a is moved down through the cavity 12a of the protection die 12 to press the mixture 3 while heating, so that the resultant calcium phosphate-synthetic resin composite body adheres to the metal member (metal screw body) 200. FIG. 28(b) shows a state where the molding is completed.

Figure 29:
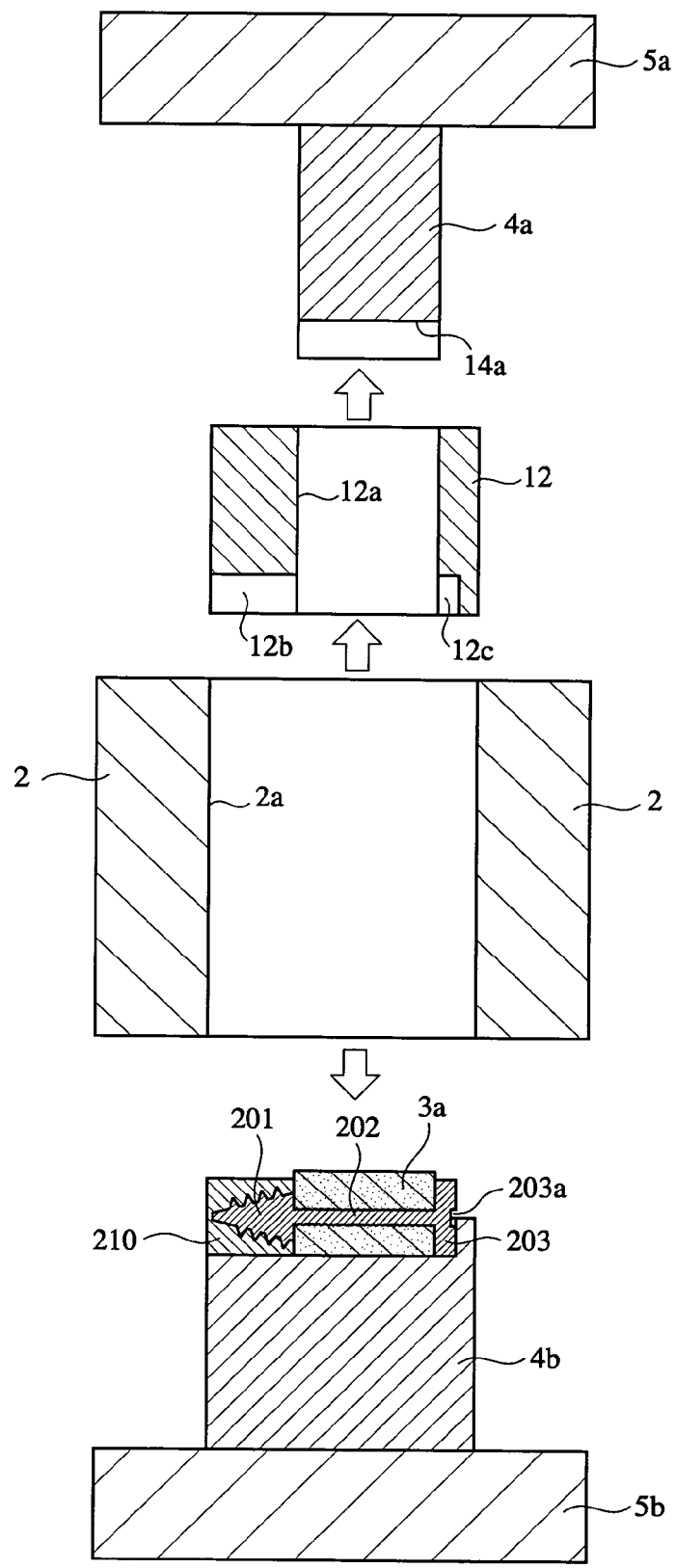
FIG. 29 is a vertical cross-sectional view showing a state in which the molding is taken out from the molding die after pressing and heating.
Figure 30:
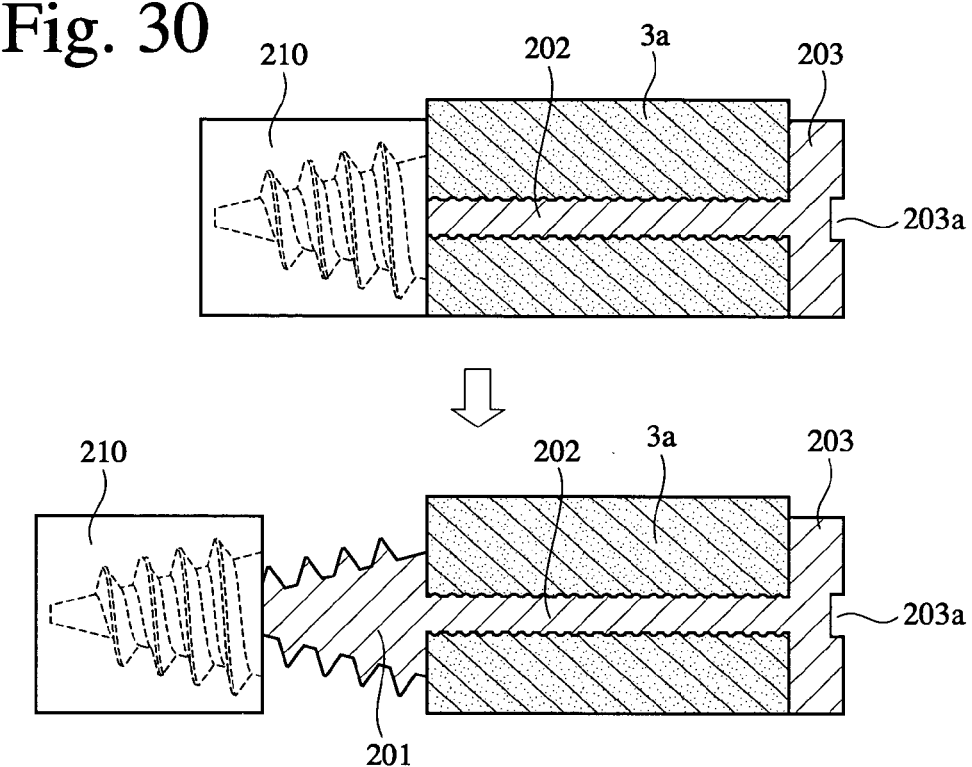
FIG. 30 is a cross-sectional view showing the removal of the cap from the molded product.

After the completion of molding, as shown in FIG. 29, the upper and lower punches 4a, 4b and the protection die 12 are moved outward from the stationary die member 2, and the resultant screw-shaped composite body comprising the screw metal 200 and the calcium phosphate-synthetic resin composite layer 3a adhering to the screw metal 200 is removed from the lower punch 4b. As shown in FIG. 30, the calcium phosphate-synthetic resin composite layer 3a adheres only to the screw trunk 202 but not to the cap 210 and the head 203. Accordingly, the cap 210 can be easily detached form the screw metal 200 by rotation. The detached cap 210 is reused in subsequent molding steps after coating a parting agent again.

Figure 31:
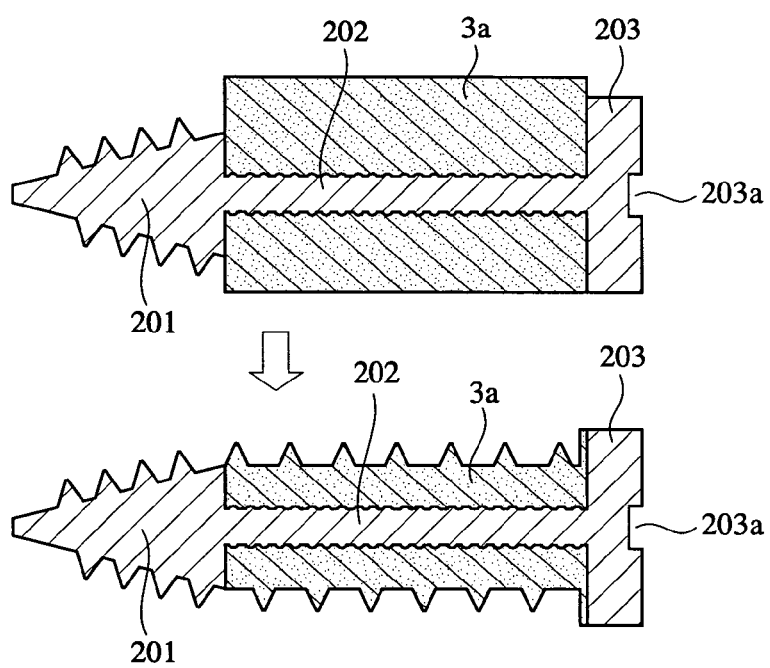
FIG. 31 is a cross-sectional view showing the threading of the cap-detached molded product.

As shown in FIG. 31, with the head 203 gripped, the calcium phosphate-synthetic resin composite body around the trunk 202 is ground to a screw shape. The calcium phosphate-synthetic resin composite body 3a is ground in a limited area slightly inside the head 203 to permit a grinding error. Though the calcium phosphate-synthetic resin composite body 3a is slightly left on the inside surface of the head 203, it can easily be removed.

The present invention will be explained in more detail by the following Examples without intention to limit the present invention thereto.

EXAMPLE 1

10 g of calcium phosphate powder having an average particle diameter of 30 μm was added to 20 g of an aqueous solution containing 1% by mass of methylcellulose, and blended at a predetermined speed for a predetermined period of time. The resultant foamed slurry was molded in a molding die frame, dried at 80° C. for 72 hours and then sintered in an air furnace at 1200° C. for 4 hours. Machining was carried out to provide a calcium phosphate block 300 having a calcium/phosphorus molar ratio of 1.67, an outer shape of 20 mm in diameter and 4 mm in thickness and a porosity of 45%.

10.0 g of porous calcium phosphate particles 100 having particle diameters of 0.2 to 0.6 mm and a calcium/phosphorus molar ratio of 1.67, which was sintered in an air furnace at 1200° C., 4.0 g of cross-linked acrylic powder I having an average particle diameter of 3.0 μm (Chemisnow MX-300 available from Soken Chemical & Engineering Co., Ltd.), and 1.0 g of uncross-linked acrylic powder II having an average particle diameter of 1.5 μm (Chemisnow MP-1400 available from Soken Chemical & Engineering Co., Ltd.) were mixed.

To obtain the calcium phosphate-synthetic resin-metal composite body having the structure shown in FIG. 1, a circular stainless steel plate 200 (20 mm in diameter and 8 mm in thickness), 2.2 g of a mixture of the porous calcium phosphate particles 100 and the synthetic resin particles I and II, and a circular, plate-like, porous calcium phosphate block 300 (20 mm in diameter×4 mm in thickness) were charged into the cavity 2a of the stationary die member 2 (20 mm in internal diameter×50 mm in height) in the pressing/heating apparatus shown in FIGS. 16 to 18. The mixture in the die cavity 2a was kept at a temperature of 240° C. for 10 minutes while pressing at a pressure of 10 MPa from above and below. It was then cooled, and the pressure was released at room temperature.

The resultant calcium phosphate-synthetic resin-metal composite body was machined by a lathe to obtain a composite body with a diameter of 20 mm and a thickness of 15.7 mm. The observation of a surface of the calcium phosphate-synthetic resin composite layer 3a of this composite body by a scanning electron microscope revealed that the calcium phosphate was exposed on the surface without being covered with the acrylic resin.

EXAMPLE 2

To obtain the calcium phosphate-synthetic resin-metal composite body having the structure shown in FIG. 2, a sintered body was prepared in the same manner as in Example 1, except for changing the blending speed and time of a mixture of an aqueous methylcellulose solution and calcium phosphate powder to change the porosity. The sintered body was machined to produce a cylindrical, porous calcium phosphate block 300 having a molar ratio of calcium to phosphorus of 1.67 with an external diameter of 20 mm, an internal diameter of 16 mm and a thickness of 15 mm and with a porosity of 30%.

The above cylindrical, porous calcium phosphate block 300, a stainless steel column 200 (10 mm in diameter×15 mm in thickness), and 3.40 g of a mixture of porous calcium phosphate particles and the synthetic resin particles I and II, which was obtained in the same manner as in Example 1, were charged into the cavity 2a of the stationary die member 2 (20 mm in internal diameter×50 mm in height) of the pressing/heating apparatus shown in FIGS. 16 to 18. The content in the cavity 2a of the stationary die member 2 was kept at a temperature of 200° C. for 5 minutes while pressing at a pressure of 5 MPa from above and below. It was then cooled, and the pressure was released at room temperature.

The resultant calcium phosphate-synthetic resin-metal composite body was machined by a lathe to obtain a composite body with a diameter of 20 mm and a thickness of 15 mm. The observation of a surface of the calcium phosphate-synthetic resin composite layer 3a of this composite body by a scanning electron microscope revealed that the calcium phosphate was exposed on the surface without being covered with the acrylic resin.

EXAMPLE 3

To obtain the calcium phosphate-synthetic resin-metal composite body having the structure shown in FIG. 9, a cylindrical stainless steel member 200 (15 mm in external diameter, 10 mm in internal diameter, 10 mm in thickness), and 1.40 g of a mixture of the porous calcium phosphate particles and the synthetic resin particles I and II, which was obtained in the same manner as in Example 1, were charged into the cavity 2a of the stationary die member 2 (15 mm in internal diameter×30 mm in height) of the pressing/heating apparatus shown in FIGS. 16 to 18. The content in the molding die cavity 2a was kept at a temperature of 180° C. for 10 minutes while pressing at a pressure of 10 MPa from above and below. It was then cooled, and the pressure was released at room temperature.

The calcium phosphate-synthetic resin composite layer 3a adhering to the top surface of the cylindrical stainless steel member 200 was removed by machining to obtain the composite body. The observation by scanning electron microscope revealed that the calcium phosphate was exposed on the surface without being covered with the acrylic resin.

EXAMPLE 4

To produce a bone-connecting screw used as a biomaterial, as shown in FIG. 15, a cap 210 (7.0 mm in external diameter, 10.0 mm in entire length) was put onto a thread 201 of a stainless steel screw 200 (6.0 mm in external diameter at the root of a thread 201, 30.0 mm in entire length, 3.0 mm in external diameter of a trunk 202, 7.0 mm in external diameter of a head 203) shown in FIG. 23. With the stainless steel screw 200 provided with the cap 210 placed in a semicylindrical cavity 14b (32.0 mm in length× 3.5 mm in radius) of a lower punch 4b, the lower punch 4b was moved up, so that the stainless steel screw 200 was fixed around the center in the cavity 2a of the stationary die member 2 of the pressing/heating apparatus. In the state shown in FIG. 27, a protection die 12 was moved down to abut the cap 210, and 1.30 g of a mixture of the porous calcium phosphate particles and the synthetic resin particles I and II, which was obtained in the same manner as in Example 1, was then charged into the cavity 14b of the lower punch 4b and in the cavity 12a of the protection die 12.

As shown in FIG. 28, the upper punch 4a was moved down, and the mixture 3a charged into the cavity 2a was kept at a temperature of 200° C. for 10 minutes while pressing at a pressure of 10 MPa. The mixture 3a was then cooled, and the upper and lower punches and the protection die 12 were moved outside the stationary die member 2 to take out the resultant molded product.

After the cap 210 was detached from the molded product as shown in FIG. 30, the calcium phosphate-synthetic resin composite layer 3a was machined to a screw shape as shown in FIG. 31 to obtain the composite body shown in FIG. 15. The observation of a surface of the calcium phosphate-synthetic resin composite layer 3a of this composite body by a scanning electron microscope revealed that the calcium phosphate was exposed on the surface without being covered with the acrylic resin.

EXAMPLE 5

(1) Preparation of Mixture 10 g of the porous calcium phosphate particles 100 having an average particle diameter of 0.2 to 0.6 mm and a calcium/phosphorus molar ratio of 1.67 was sintered in an air furnace at 1,200° C., 4 g of cross-linked acrylic powder I having an average particle diameter of 3 μm (Chemisnow MX-300 available from Soken Chemical & Engineering Co., Ltd.), and 1 g of uncross-linked acrylic powder II having an average particle diameter of 1.5 μm (Chemisnow MP-1400 available from Soken Chemical & Engineering Co., Ltd.) were mixed.

(2) Charging into Molding Die

As shown in FIG. 20, the mixture 3 prepared in the above step (1) was charged into the cavity 2a (24 mm×14 mm×50 mm in height) of the stationary die member 2 in the pressing/heating apparatus to a height of approximately 7 mm, a titanium member 200 (20.0 mm×10.0 mm×15 mm in height, 2.0 mm in thickness) having the structure shown in FIG. 12 having windows (5.0 mm×8.0 mm) was placed on the mixture 3, and then the rest of the mixture 3 was charged into the cavity 2a such that it entered into space inside and outside the titanium member 200. The titanium member 200 was thus embedded in the mixture 3.

(3) Pressing/Heating Treatment

The content in the cavity 2a was kept at a temperature of 200° C. for 5 minutes while pressing from above and below at a pressure of 10 MPa, and then cooled to room temperature, and the pressure was released. In the resultant cylindrical metal member-embedded composite body 400, the metal member 200 was filled with the calcium phosphate-synthetic resin composite body without gap. The calcium phosphate-synthetic resin composite body of the cylindrical metal member-embedded composite body 400 was machined to the calcium phosphate-synthetic resin composite layer 3a having a thickness of about 1 mm by a milling machine with a machining center, thereby providing the calcium phosphate-synthetic resin-metal composite body (22.0 mm×12.0 mm×17 mm in height, 4.0 mm in thickness) having windows (3.0 mm×6.0 mm) as shown in FIGS. 13 and 14. The observation of a surface of the calcium phosphate-synthetic resin composite layer 3a of this composite body by a scanning electron microscope revealed that the calcium phosphate was exposed on the surface without being covered with the acrylic resin. Because the metal member was completely covered with the calcium phosphate-synthetic resin composite layer, it was not exposed on the surface of the composite body.

EXAMPLE 6

(1) Preparation of Mixture 6 g of the porous calcium phosphate particles 100 having an average particle diameter of 0.1 to 0.3 mm and a calcium/phosphorus molar ratio of 1.50, which was sintered in an air furnace at 700° C., 6 g of cross-linked acrylic powder I having an average particle diameter of 3 μm (Chemisnow MX-300 available from Soken Chemical & Engineering Co., Ltd.), and 0.5 g of uncross-linked acrylic powder II having an average particle diameter of 1.5 μm (Chemisnow MP-1400 available from Soken Chemical & Engineering Co., Ltd.) were mixed.

(2) Charging into Molding Die

After the mixture 3 prepared in the step (1) was charged into the cavity 2a (30 mm×40 mm×30 mm in height) of the stationary die member 2 of the pressing/heating apparatus to a height of approximately 6 mm, a titanium net (wire diameter: 1.0 mm, 8 meshes, 25.0 mm×35.0 mm) was placed thereon, and the rest of the mixture 3 was added thereon.

(3) Pressing/Heating Treatment

The content in the cavity 2a was kept at a temperature of 200° C. for 5 minutes while pressing at a pressure of 10 MPa from above and below. It was then cooled, and the pressure was released at room temperature. The resultant calcium phosphate-synthetic resin composite body was worked by a milling machine to a calcium phosphate-synthetic resin composite layer 3a of about 1 mm in thickness, thereby obtaining a calcium phosphate-synthetic resin-metal composite body shown in FIG. 10 (27.0 mm×37.0 mm×2.5 mm in thickness). The observation of a surface of the calcium phosphate-synthetic resin composite layer 3a of this composite body by a scanning electron microscope revealed that the calcium phosphate was exposed on the surface without being covered with the acrylic resin. This composite body was sterilized at 121° C. for 20 minutes in an autoclave. The three-point bending strength of this calcium phosphate-synthetic resin-metal composite body was 77.6 MPa. Because the metal member was completely covered with the calcium phosphate-synthetic resin composite layer, it was not exposed on the surface of the body.

COMPARATIVE EXAMPLE 1

A calcium phosphate-synthetic resin composite body was produced in the same manner as in Example 6 except for using no titanium net. The three-point bending strength of the resultant composite body was 25.5 MPa.

As described above, the calcium phosphate-synthetic resin-metal composite body of the present invention has high biocompatibility and mechanical strength, because the calcium phosphate particles and/or the calcium phosphate block having excellent biocompatibility are exposed on at least part of the surface of the composite body, and because it comprises a metal member having excellent mechanical strength. The calcium phosphate-synthetic resin-metal composite body of the present invention having such a structure is excellent in workability, biocompatibility, water resistance and impact resistance, and suitable for artificial dental roots, bone reinforcements, etc. The present disclosure relates to subject matter contained in Japanese Patent Application Nos. 2002-211690 (filed on Jul. 19, 2002) and 2003-176747 (filed on Jun. 20, 2003) which are expressly incorporated herein by reference in its entirety.

What is claimed is:

1. A calcium phosphate-synthetic resin-metal composite body produced by pressing a metal member, a calcium phosphate block and a mixture of calcium phosphate particles, synthetic resin particles I, which are at least partially cross-linked in advance, and uncross-linked, synthetic resin particles II while heating, said calcium phosphate particles and/or said calcium phosphate block being exposed on at least part of the surface of said composite body, wherein said synthetic resin particles I and II are bonded to said metal member, said calcium phosphate particles and said calcium phosphate block.

2. The calcium phosphate-synthetic resin-metal composite body according to claim 1, wherein said calcium phosphate-synthetic resin-metal composite body comprises a calcium phosphate-synthetic resin composite layer composed of said calcium phosphate particles and said synthetic resin particles I and II, which covers the entire surface of said metal member.

3. The calcium phosphate-synthetic resin-metal composite body according to claim 1, wherein said metal member is made of at least one metal or alloy selected from the group consisting of pure titanium, titanium alloys and stainless steel.

4. The calcium phosphate-synthetic resin-metal composite body according to claim 1, wherein said synthetic resin particles I and II are made of a water-insoluble acrylic or polystyrene resin.

5. The calcium phosphate-synthetic resin-metal composite body according to claim 1, wherein said calcium phosphate particles and/or said calcium phosphate block are sintered.

6. The calcium phosphate-synthetic resin-metal composite body according to claim 1, wherein said calcium phosphate particles and said calcium phosphate block are porous.

7. The calcium phosphate-synthetic resin-metal composite body according to claim 1, wherein at least part of said metal member has a thickness of 0.5 mm or more.

8. The calcium phosphate-synthetic resin-metal composite body according to claim 1, wherein the content of said synthetic resin particles II is 0.2 to 50% by mass based on the total amount of said synthetic resin particles I and II.

9. The calcium phosphate-synthetic resin-metal composite body according to claim 1, wherein a mass ratio of said calcium phosphate particles to said synthetic resin particles is 1/9 to 8/2.

10. The calcium phosphate-synthetic resin-metal composite body according to claim 1, wherein a calcium/phosphorus molar ratio in said calcium phosphate particles and said calcium phosphate block is 1.4 to 2.0.

11. The calcium phosphate-synthetic resin-metal composite body according to claim 1, wherein said calcium phosphate particles have an average particle size of 0.001 to 10 mm.

12. The calcium phosphate-synthetic resin-metal composite body according to claim 1, wherein said calcium phosphate block has a thickness of 1 mm or more.

13. A calcium phosphate-synthetic resin-metal composite body produced by pressing a metal member and a mixture of calcium phosphate particles, synthetic resin particles I, which are at least partially cross-linked in advance, and uncross-linked, synthetic resin particles II while heating, said calcium phosphate particles being exposed on at least part of the surface of said composite body, wherein said synthetic resin particles I and II are bonded to said metal member, said calcium phosphate particles and said calcium phosphate block.

14. The calcium phosphate-synthetic resin-metal composite body according to claim 13, wherein said calcium phosphate-synthetic resin-metal composite body comprises a calcium phosphate-synthetic resin composite layer composed of said calcium phosphate particles and said synthetic resin particles I and II, which covers the entire surface of said metal member.

15. The calcium phosphate-synthetic resin-metal composite body according to claim 13, wherein said metal member is made of at least one metal or alloy selected from the group consisting of pure titanium, titanium alloys and stainless steel.

16. The calcium phosphate-synthetic resin-metal composite body according to claim 13, wherein said synthetic resin particles I and II are made of a water-insoluble acrylic or polystyrene resin.

17. The calcium phosphate-synthetic resin-metal composite body according to claim 13, wherein said calcium phosphate particles are sintered.

18. The calcium phosphate-synthetic resin-metal composite body according to claim 13, wherein said calcium phosphate particles are porous.

19. The calcium phosphate-synthetic resin-metal composite body according to claim 13, wherein at least part of said metal member has a thickness of 0.5 mm or more.

20. The calcium phosphate-synthetic resin-metal composite body according to claim 13, wherein the content of said synthetic resin particles II is 0.2 to 50% by mass based on the total amount of said synthetic resin particles I and II.

21. The calcium phosphate-synthetic resin-metal composite body according to claim 13, wherein a mass ratio of said calcium phosphate particles to said synthetic resin particles is 1/9 to 8/2.

22. The calcium phosphate-synthetic resin-metal composite body according to claim 13, wherein a calcium/phosphorus molar ratio in said calcium phosphate particles is 1.4 to 2.0.

23. The calcium phosphate-synthetic resin-metal composite body according to claim 13, wherein said calcium phosphate particles have an average particle size of 0.001 to 10 mm.

24. The calcium phosphate-synthetic resin-metal composite body according to claim 13, wherein said metal member has a hollow shape; and wherein said calcium phosphate-synthetic resin composite layer covers the entire surface of said metal member.

25. The calcium phosphate-synthetic resin-metal composite body according to claim 24, wherein said metal member has windows at which said calcium phosphate-synthetic resin composite layer is open.

26. The calcium phosphate-synthetic resin-metal composite body according to claim 13, wherein said calcium phosphate-synthetic resin-metal composite body has a screw shape; and wherein a calcium phosphate-synthetic resin composite layer composed of said calcium phosphate particles and said synthetic resin particles I and II is formed on a trunk of said metal member.

27. A method for producing a calcium phosphate-synthetic resin-metal composite body comprising a metal member, calcium phosphate particles, synthetic resin particles I, which are at least partially cross-linked in advance, and uncross-linked, synthetic resin particles II, said calcium phosphate particles being exposed on at least part of the surface of said composite body, wherein said synthetic resin particles I and II are bonded to said metal member and said calcium phosphate particles, said method comprising the steps of (a) introducing said metal member, said calcium phosphate particles, and said synthetic resin particles I and II into a cavity of a molding die, such that said synthetic resin particles surround said calcium phosphate particles, and that said calcium phosphate particles are exposed on at least part of the surface of said composite body; and (b) pressing them in said molding die cavity while heating, so that said synthetic resin particles are bonded to said metal member and said calcium phosphate particles.

28. The method for producing a calcium phosphate-synthetic resin-metal composite body according to claim 27, wherein said metal member and a mixture of said calcium phosphate particles and said synthetic resin particles I and II are introduced into said cavity of said molding die such that said mixture surrounds said metal member.

29. The method for producing a calcium phosphate-synthetic resin-metal composite body according to claim 27 further comprising the step of sintering said calcium phosphate particles in advance.

30. The method for producing a calcium phosphate-synthetic resin-metal composite body according to claim 29, wherein the sintering temperature of said calcium phosphate particles block is 500° C. to 1,300° C.

31. The method for producing a calcium phosphate-synthetic resin-metal composite body according to claim 27, wherein said pressing/heating step is carried out in vacuum, or in an atmosphere containing no oxygen.

32. The method for producing a calcium phosphate-synthetic resin-metal composite body according to claim 27, comprising using a hollow metal member; heating said hollow metal member filled with said mixture while pressing to provide a metal member-embedded composite body comprising said metal member filled with a calcium phosphate-synthetic resin composite body; cutting away part of said calcium phosphate-synthetic resin composite body in said metal member-embedded composite body to make said calcium phosphate-synthetic resin-metal composite body hollow.

33. The method for producing a calcium phosphate-synthetic resin-metal composite body according to claim 32, comprising using a metal member having windows; and grinding said calcium phosphate-synthetic resin composite body at positions corresponding to said windows to provide said calcium phosphate-synthetic resin-metal composite body with windows.

34. The method for producing a calcium phosphate-synthetic resin-metal composite body according to claim 27, comprising using a screw-shaped metal member; placing said screw-shaped metal member in a cavity of said molding die with a cap mounted on a thread of said metal member; charging a mixture of said calcium phosphate particles and said synthetic resin particles I and II into said die cavity; pressing said mixture while heating to form a calcium phosphate-synthetic resin composite body around said metal member; removing said cap from said screw-shaped metal member; and machining said calcium phosphate-synthetic resin composite body around a trunk of said metal member to provide said calcium phosphate-synthetic resin-metal composite body with a threaded portion.

35. The method for producing a calcium phosphate-synthetic resin-metal composite body according to claim 34, comprising using a molding die comprising a stationary die member having a cavity penetrating in a vertical direction; a lower punch having a cavity for receiving a screw-shaped metal member provided with a cap and entering into the cavity of said stationary die member from below; a protection die having a cavity penetrating in a vertical direction and a cavity for receiving a head and said cap of said screw-shaped metal member provided with a cap and abutting said lower punch; and a vertically movable upper punch having a cavity having the same shape as that of said cavity of said lower punch at a position aligned with said cavity of said lower punch, and entering into the vertical cavity of said protection die from above to abut said lower punch.

36. The method for producing a calcium phosphate-synthetic resin-metal composite body according to claim 35, comprising placing said lower punch in said cavity of said stationary die member after said screw-shaped metal member provided with said cap is placed on said cavity of the lower punch; moving said protection die down so that said cavity of the protection die abuts said cavity of the lower punch; charging a mixture of said calcium phosphate particles and said synthetic resin particles I and II into the cavities of said lower punch and said protection die; moving said upper punch down to press said mixture while heating, thereby forming a layer of a calcium phosphate-synthetic resin composite body on a trunk of said metal member.

37. A method for producing a calcium phosphate-synthetic resin-metal composite body comprising a metal member, calcium phosphate particles and a calcium phosphate block, synthetic resin particles I, which are at least partially cross-linked in advance, and uncross-linked, synthetic resin particles II, said calcium phosphate particles and/or said calcium phosphate block being exposed on at least part of the surface of said composite body, wherein said synthetic resin particles I and II are bonded to said metal member, said calcium phosphate particles and said calcium phosphate block, said method comprising the steps of (a) introducing said metal member, said calcium phosphate particles and said calcium phosphate block, and said synthetic resin particles I and II into a cavity of a molding die, such that said synthetic resin particles surround said calcium phosphate particles, and that said calcium phosphate particles and/or said calcium phosphate block are exposed on at least part of the surface of said composite body; and (b) pressing them in said molding die cavity while heating, so that said synthetic resin particles are bonded to said metal member and said calcium phosphate particles and said calcium phosphate block.

38. The method for producing a calcium phosphate-synthetic resin-metal composite body according to claim 37, wherein said metal member and a mixture of said calcium phosphate particles and said synthetic resin particles I and II are introduced into said cavity of said molding die such that said mixture surrounds said metal member.

39. The method for producing a calcium phosphate-synthetic resin-metal composite body according to claim 37 further comprising the step of sintering said calcium phosphate particles and/or said calcium phosphate block in advance.

40. The method for producing a calcium phosphate-synthetic resin-metal composite body according to claim 39, wherein the sintering temperature of said calcium phosphate particles and said calcium phosphate block is 500° C. to 1,300° C.

41. The method for producing a calcium phosphate-synthetic resin-metal composite body according to claim 37, wherein said pressing/heating step is carried out in vacuum, or in an atmosphere containing no oxygen.

42. The method for producing a calcium phosphate-synthetic resin-metal composite body according to claim 37, comprising using a hollow metal member; heating said hollow metal member filled with said mixture while pressing to provide a metal member-embedded composite body comprising said metal member filled with a calcium phosphate-synthetic resin composite body; cutting away part of said calcium phosphate-synthetic resin composite body in said metal member-embedded composite body to make said calcium phosphate-synthetic resin-metal composite body hollow.

43. The method for producing a calcium phosphate-synthetic resin-metal composite body according to claim 42, comprising using a metal member having windows; and grinding said calcium phosphate-synthetic resin composite body at positions corresponding to said windows to provide said calcium phosphate-synthetic resin-metal composite body with windows.

44. The method for producing a calcium phosphate-synthetic resin-metal composite body according to claim 37, comprising using a screw-shaped metal member; placing said screw-shaped metal member in a cavity of said molding die with a cap mounted on a thread of said metal member; charging a mixture of said calcium phosphate particles and said synthetic resin particles I and II into said die cavity; pressing said mixture while heating to form a calcium phosphate-synthetic resin composite body around said metal member; removing said cap from said screw-shaped metal member; and machining said calcium phosphate-synthetic resin composite body around a trunk of said metal member to provide said calcium phosphate-synthetic resin-metal composite body with a threaded portion.

45. The method for producing a calcium phosphate-synthetic resin-metal composite body according to claim 44, comprising using a molding die comprising a stationary die member having a cavity penetrating in a vertical direction; a lower punch having a cavity for receiving a screw-shaped metal member provided with a cap and entering into the cavity of said stationary die member from below; a protection die having a cavity penetrating in a vertical direction and a cavity for receiving a head and said cap of said screw-shaped metal member provided with a cap and abutting said lower punch; and a vertically movable upper punch having a cavity having the same shape as that of said cavity of said lower punch at a position aligned with said cavity of said lower punch, and entering into the vertical cavity of said protection die from above to abut said lower punch.

46. The method for producing a calcium phosphate-synthetic resin-metal composite body according to claim 45, comprising placing said lower punch in said cavity of said stationary die member after said screw-shaped metal member provided with said cap is placed on said cavity of the lower punch; moving said protection die down so that said cavity of the protection die abuts said cavity of the lower punch; charging a mixture of said calcium phosphate particles and said synthetic resin particles I and II into the cavities of said lower punch and said protection die; moving said upper punch down to press said mixture while heating, thereby forming a layer of a calcium phosphate-synthetic resin composite body on a trunk of said metal member.

47. The calcium phosphate-synthetic resin-metal composite body according to claim 13, wherein the synthetic resin particles I are softened while retaining their shapes to some extent, whereas the uncross-linked, synthetic resin particles II having thermoplasticity are softened or melted during pressing while heating.

* * * * *